(12) United States Patent
Sibi et al.

(10) Patent No.: US 11,220,475 B2
(45) Date of Patent: Jan. 11, 2022

(54) MONOMERS FROM BIOMASS

(71) Applicants: Mukund P. Sibi, Fargo, ND (US);
Selvakumar Sermadurai, Kyoto (JP);
Nicolas Zimmermann, Treillères (FR);
Eric Serum, Eau Claire, WI (US);
Gaoyuan Ma, Irvine, CA (US);
Ramkumar Moorthy, Saint Paul, MN (US); Krystal Kalliokoski, Fargo, ND (US)

(72) Inventors: Mukund P. Sibi, Fargo, ND (US);
Selvakumar Sermadurai, Kyoto (JP);
Nicolas Zimmermann, Treillères (FR);
Eric Serum, Eau Claire, WI (US);
Gaoyuan Ma, Irvine, CA (US);
Ramkumar Moorthy, Saint Paul, MN (US); Krystal Kalliokoski, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 14 days.

(21) Appl. No.: 16/722,710

(22) Filed: Dec. 20, 2019

(65) Prior Publication Data

US 2020/0140368 A1 May 7, 2020
US 2021/0198175 A9 Jul. 1, 2021

Related U.S. Application Data

(62) Division of application No. 15/502,653, filed as application No. PCT/US2015/044260 on Aug. 7, 2015, now Pat. No. 10,513,482.

(60) Provisional application No. 62/035,197, filed on Aug. 8, 2014.

(51) Int. Cl.
| | | |
|---|---|---|
| *C07C 57/34* | (2006.01) | |
| *C07C 57/40* | (2006.01) | |
| *C07C 59/84* | (2006.01) | |
| *C08G 63/181* | (2006.01) | |
| *C07C 59/64* | (2006.01) | |
| *C07D 307/54* | (2006.01) | |
| *C08G 63/06* | (2006.01) | |

(52) U.S. Cl.
CPC ............. *C07C 57/34* (2013.01); *C07C 57/40* (2013.01); *C07C 59/64* (2013.01); *C07C 59/84* (2013.01); *C07D 307/54* (2013.01); *C08G 63/065* (2013.01); *C08G 63/181* (2013.01)

(58) Field of Classification Search
CPC ......... C07C 57/34; C07C 57/40; C07C 59/64; C07C 59/84; C08G 63/181; C08G 63/065; C07D 307/54
USPC ...................................................... 524/600
See application file for complete search history.

(56) References Cited

U.S. PATENT DOCUMENTS

| | | | |
|---|---|---|---|
| 4,221,725 A | 9/1980 | Bernstein et al. | |
| 4,977,283 A | 12/1990 | Leupold et al. | |
| 6,252,025 B1 | 6/2001 | Wang et al. | |
| 9,738,753 B2 * | 8/2017 | Sivaguru | C07D 307/68 |
| 2007/0232815 A1 * | 10/2007 | Miura | C07D 307/48 549/485 |
| 2008/0033188 A1 * | 2/2008 | Dumesic | C07D 307/46 549/505 |
| 2009/0156841 A1 * | 6/2009 | Sanborn | C07D 307/50 549/488 |
| 2013/0066116 A1 | 3/2013 | Goettmann et al. | |
| 2013/0115653 A1 | 5/2013 | Peterson et al. | |
| 2014/0107355 A1 * | 4/2014 | Dumesic | C07D 307/50 549/485 |
| 2017/0233325 A1 | 8/2017 | Sibi et al. | |

OTHER PUBLICATIONS

S. Bauer et al. "Furancarboxylic Acids in Cattle Urine", Furancarbonsauren aus Rinderharn. HCA, 68, (1985), pp. 1635-1638. (Year: 1985).*
International Search Report and Written Opinion for International Patent Application No. PCT/US2015/044260, dated Mar. 28, 2016, 14 pages.
International Preliminary Report on Patentability for International Patent Application No. PCT/US2015/044260, dated Feb. 14, 2017, 11 pages.
Amir et al., "Structural characterization of humic acids, extracted from sewage sludge during composting, by thermochemolysis-gas chromatography-mass spectrometry," *Process Biochemistry*, Feb. 2006; 41(2):410-422.
Aziz ur Rahman et al., "Studien uber doppelte Acylierung von Aromaten, III. Synthese von Triphenylen durch doppelte Succinylierung von Naphthalin," *Chemische Berichte*, Jun. 6, 1966; 99(6): 1805-1809.
Balakrshnan et al., "Etherification and reductive etherification of 5-(hydroxymethyl) furfural: 5-(alkoxymethyl) furfurals and 2, 5-bis(alkoxymethyl)furans as potential bio-diesel candidates," *Green Chemistry*, Mar. 19, 2012; 14(6): 1626-1634.
Belgacem et al., "Monomers, Polymers and Composites from Renewable Resources," Elsevier, Amsterdam, The Netherlands, First Edition 2008.
Bickley et al., "Dirhodium (II) carboxylate complexes as building blocks, cis-Chelating dicarboxylic acids designed to bridge the dinuclear core," *New. J. Chem.* 2004; 28:425-433.
Binder et al., "Simple Chemical Transformation of Lignocellulosic Biomass into Furans for Fuels and Chemicals," *J. Am. Chem. Soc.* Jan. 21, 2009; 131(5): 1979-1985.
Blommel, "Catalytic Conversion of Carbohydrates to Hydrocarbons," Virent, DOE Biomass R&D TAC Meeting, May 19, 2011.
Costa et al., "New noncellular fluorescence microplate screening assay for scavenging activity against singlet oxygen," *Analytical and Bioanalytical Chemistry*, Jan. 17, 2007; 387(6):2071-2081.
Dodds and Gross, "Chemicals from Biomass," *Science Perspectives*, Nov. 23, 2007;318:1250-1.

(Continued)

*Primary Examiner* — Michael M. Bernshteyn
(74) *Attorney, Agent, or Firm* — Mueting Raasch Group

(57) ABSTRACT

Compounds derived from biomass, e.g., cellulose and lignins, methods of forming such compounds and polymers and products formed using such compounds.

31 Claims, No Drawings

(56) References Cited

OTHER PUBLICATIONS

Gallo et al., "Production and upgrading of 5-hydroxymethylfurfural using heterogenous catalysts and biomass-derived solvents," *Green Chemistry*, Oct. 26, 2013; 15(1):85-90.
Gandini, "Polymers from Renewable Resources: A Challenge for the Future of Macromolecular Materials," *Macromolecules*, Dec. 23, 2008, 41(24):9491-9504.
Gung et al., "Transannular [4C+3C]-Cycloaddition Reactions of Oxyallyl Cation to Furan," *Synlett*, Oct. 8, 2010; 18:2797-2801.
Huber et al., "Synthesis of Transportation Fuels from Biomass: Chemistry, Catalysts, and Engineering," *Chem. Rev.*, 2006, 106(9):4044-4098.
Ishichi et al., "Novel triple reuptake inhibitors with low risk of CAD associated liabilities: Design, synthesis and biological activities of 4-[(1S)-1-(3,4-dichlorophenyl)-2-methoxyethyl]piperidine and related compounds," *J. Bioorg. Med. Chem.*, Aug. 1, 2013; 21(15):4600-4613.
Kalliokoski et al., "Synthesis of monomers from hydroxymethyl furfural and furan dicarboxylic acid," NDSU, presented at EPSCOR meeting Apr. 2014.
Lange et al., "Oxidative upgrade of lignin—Recent routes reviewed," *European Polymer Journal*, 2013; 49:1151-1173.
Liao and Liu, "Diamination of Phenylene Dihalides Catalyzed by a Dicopper Complex," *The Journal of Organic Chemistry*, 2012; 77:6653-6656.
Lichtenthaler et al., "Carbohydrates as green raw materials for the chemical industry," *C.R. Chemie 7*, 2004; 65-90.
Lichtenthaler et al., "Carbohydrate-based Product Lines: Chapter 1—The Key Sugars of Biomass: Availability, Present Non-Food Uses and Potential Future Development Lines," *Biorefineries—Industrial Processes and Products: Status Quo and Future Directions*, vol. 2, Wiley, 2008.
McDermott et al., "Combining two-directional synthesis and tandem reactions: synthesis of trioxadispiroketals," *Organic Letters*, Dec. 9, 2004; 7(1):27-29.
PubChem CID 28930983, Feb. 9, 2007, 1-10.
PubChem CID 317429, Feb. 3, 2005, 1-11.
PubChem CID 14662358, May 28, 2009, 1-10.
Rau et al., "Tetrahydrofuransaureneine neue Klasse von Verbindungen des Humanstoffwechsels," *Liebiegs Analen der Chemie*, Aug. 10, 1984; 8:1504-1512.
Skowroński et al., "New Chemical Conversions of 5-Hydroxymethylfurfural and the Electrochemical Oxidation of Its Derivatives," *Org. Prep. Proced. Int.*, 1993; 25(3):353-5.
Steurer et al., "Aminoalkyl-Substituted α-Methylene-γ-butyrolactones from α-Amino Acids Using an Indium-Mediated Barbier Allyl Addition," *J. Eur. J. Org. Chem.*, Jun. 14, 1999; 1999(7): 1551-11560.
Tang et al., "Synthesis and characterization of derivatized capped porphyrins," *Can. J. Chem.*, May 5, 1992; 70:1366-1374.
"Top Value Added Chemicals From Biomass, vol. 1: Results of Screening for Potential Candidates From Sugars and Synthesis Gas," Aug. 2004, Pacific Northwest National Laboratory.
"Top Value Added Chemicals from Biomass, vol. II: Results of Screening for Potential Candidates from Biorefinery Lignin," Oct. 2007, Pacific Northwest National Laboratory.
Vlachos, "Plastics from Renewable Sources," *J Chem Eng Process Technol*, Aug. 2012; 3:5, 1000e108.
Wiberg et al., "Preparation and Diels-Alder reactions of the [n](1,4)naphthalenophanes. Isolation of a paddlane derivative containing the tricyclo[14.2.2.2. 1,6]docosane ring system," *Journal of the American Chemical Society*, Oct. 24, 1979; 101(22):6660-6.
Zhu et al., "Diastereoselective Reductive Ring Expansion of Spiroketal Dihydropyranones to cis-Fused Bicyclic Ethers," *Organic Letters*, Nov. 19, 2012; 14(23):5892-5895.

\* cited by examiner

MONOMERS FROM BIOMASS

This application is a divisional of U.S. patent application Ser. No. 15/502,653, filed Feb. 8, 2017, which is the § 371 U.S. National Stage of International Application No. PCT/US2015/044260, filed Aug. 7, 2015, which claims the benefit of U.S. Provisional Application No. 62/035,197, filed Aug. 8, 2014, which are incorporated herein by reference in their entireties.

GOVERNMENT FUNDING

This invention was made with government support under Grant Nos. EPS-0814442, IIA-1330840, and IIA-1330842 awarded by National Science Foundation. The government has certain rights in the invention.

BACKGROUND

Approximately 96% of the organic chemicals currently used are derived from nonrenewable fossil fuels. With a dwindling oil supply, discovering alternative solutions to produce these chemicals is becoming increasingly important. One viable alternative to fossil fuels is to use biomass, a renewable resource, as a chemical feedstock. Biomass offers a carbon neutral source of organic molecules.

Lignocellulosic biomass is primarily composed of three biopolymers: cellulose, hemicelluloses and lignin. The majority of biomass polymers, when broken down into their constituents, consist of cellulose-derived sugars of 5 or 6 carbon atoms and lignin-derived aromatic building blocks. These building blocks are relatively highly oxidized and thus, without further chemical conversion, are not well-suited for fuels and chemicals. Therefore, there remains a need for novel products of biomass that can be used as feedstocks for chemical synthesis.

SUMMARY

In one aspect, the present disclosure provides compounds that are formed from biomass such as cellulose, hemicellulose and lignin. Disclosed compounds can be utilized as is, can be further modified, can be converted in polymers and various products made thereof, or any combination thereof.

Some embodiments include compounds derived from lignin. Compounds of formulae I, and IV can be derived from lignins.

Some embodiments include compounds derived from cellulose, hemicellulose, or combinations thereof. Compounds of formulae II, III, and V can be derived from cellulose, hemicellulose, or combinations thereof.

Some embodiments include compounds of formula I:

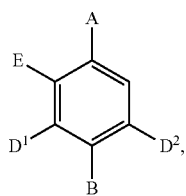

where

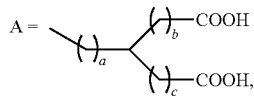

where a is 1, 2 or 3; and b and c are independently 0, 1, 2, or 3;

B is A, —OH, or —OR where R is —$CH_3$, —$CH_2CH_3$, $CH_2CH_2CH_3$, $CHCH_2$, $CHCHCH_3$, or $CH_2CHCH_2$;

$D^1$ and $D^2$ are independently H, —OH, or —OR where R is —$CH_3$, —$CH_2CH_3$, $CH_2CH_2CH_3$, $CHCH_2$, $CHCHCH_3$, or $CH_2CHCH_2$; and E is H or together with $D^1$ and the phenyl ring attached thereto forms a naphthalene ring, with the proviso that if a is 1, b is 1, c is 0, $D^2$ is —$OCH_3$, B is —OH, then $D^1$ is not H.

Some embodiments include compounds of formula II:

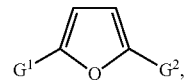

where $G^1$ and $G^2$ are independently

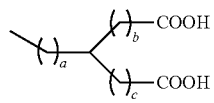

where a is 1, 2 or 3; and b and c are independently 0, 1, 2, or 3,

—$(CH_2)_d$OH where d is 1, 2, 3, 4 or 5, or

—$(CH_2)_e$COOH where e is 0, 1, 2, 3, 4 or 5, with the caveat that if both $G^1$ and $G^2$ are —$(CH_2)_e$COOH and one of e is 2 then the other e is not 0 or 2.

Some embodiments include compounds of formula III:

$$HOOC(CH_2)_f\text{-}J\text{-}(CH_2)_g COOH \quad (III),$$

where J is selected from:

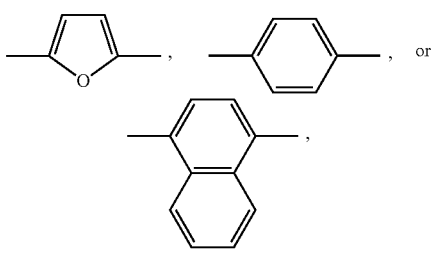

and f is 3, 4 or 5 and g is 0, 3, 4 or 5.

Some embodiments include compounds of formula IV:

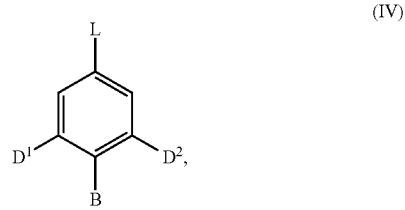

where L is —(CH$_2$)$_h$COOH, where h is 4, 5, or 6,

B is —OH, or —OR where R is —CH$_3$, —CH$_2$CH$_3$, CH$_2$CH$_2$CH$_3$, CHCH$_2$, CHCHCH$_3$, or CH$_2$CHCH$_2$;

D$^1$ and D$^2$ are independently H, —OH, or —OR where R is —CH$_3$, —CH$_2$CH$_3$, CH$_2$CH$_2$CH$_3$, CHCH$_2$, CHCHCH$_3$, or CH$_2$CHCH$_2$.

Some embodiments include compounds of formula V:

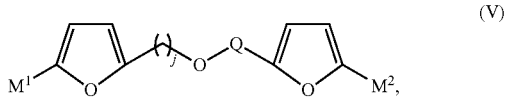

where M$^1$ and M$^2$ are independently —(CH$_2$)$_k$OH where k is 2, 3, or 4, (CH$_2$)$_m$O(CH$_2$)$_n$NH$_2$ where m an n are integers from 1 to 10;

j is 1, 2, or 3; and

Q is —(CH$_2$)$_p$ where p is 1, 2 or 3, or —(CH$_2$)$_q$O(CH$_2$)$_r$ where q and r are independently an integer from 1 to 10.

Also disclosed herein are methods for the conversion of renewable resources (e.g., lignin, cellulose, hemicellulose, or combinations thereof) to feedstock chemicals that can be used in polymer synthesis. Lignin and cellulose degradation products can be converted to higher quality monomers through chemical reactions as described herein. Any biomass source can be utilized to synthesize monomers. Moreover, the methods can be extended to compounds obtainable from other biorenewable resources such as corn starch and sugar cane.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Biomass, or more particularly lignocellulosic biomass includes, primarily, three types of biopolymers: cellulose, hemicellulose and lignin.

Cellulose is the most abundant renewable carbon source. Cellulose can be chemically described as a polymer of β-(1,4)-glucan, which has a degree of polymerization from about 300 to about 15,000. Hemicellulose can be chemically described as a short-chain branched, substituted polymer of sugars, which has a degree of polymerization from about 70 to about 200.

Lignin is an organic substance which meshes cells, fibers and vessels of wood and the woody elements of plants. It is the second most abundant renewable carbon source after cellulose, and is a mostly non-commercialized waste product. Lignin can be chemically described as a polymer derived from coniferyl, coumaryl, and sinapyl alcohol.

Disclosed herein are compounds derived from biomass (including cellulose, hemicellulose and lignins), methods of forming compounds from biomass, polymers containing the disclosed compounds, products containing the disclosed polymers, and combinations thereof.

Lignins

Disclosed herein are compounds that are specifically obtained from lignins. Lignin is a polymer and depolymerization thereof yields a variety of substituted phenols, of which p-coumaryl alcohol, coniferyl alcohol and sinapyl alcohol are the most abundant. Important, well-known phenolic derivatives of these compounds include vanillin, eugenol, iso-vanillin, isoeugenol, caffeic acid and syringeugenol. In addition to the phenolic hydroxyl, these lignin derived monomers advantageously contain an additional functionality such as an aldehyde, an allyl or isoallyl. Other lignin-derived monomers that can serve as starting materials include creosol and guaiacol. Some lignin monomers are shown below:

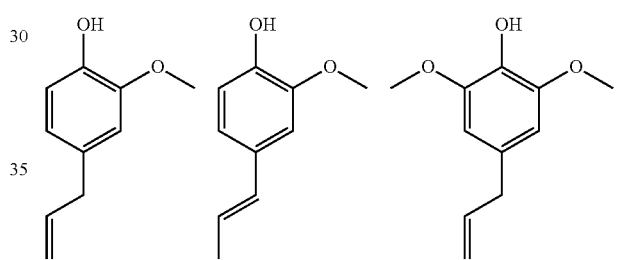

Eugenol          Isoeugenol          Syringeugenol

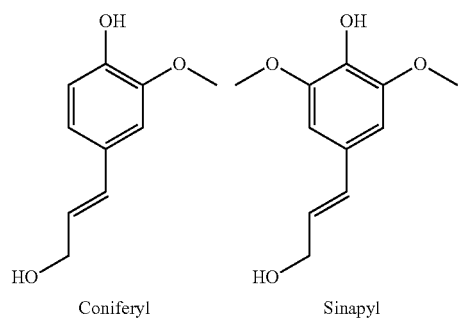

Coniferyl Alcohol          Sinapyl Alcohol

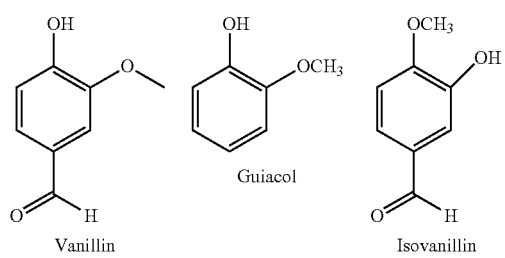

Vanillin          Guiacol          Isovanillin

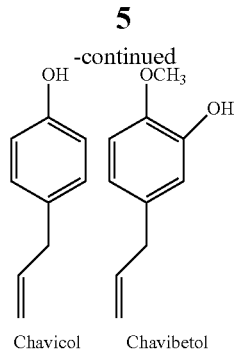

Chavicol    Chavibetol

Illustrative starting materials for the synthesis of disclosed compounds can include not only phenols but also guaiacols, syringols, eugenols, catechols, their oxidized products, including vanillin, vanillic acid, syringaldehyde, and their easily-derived hydrocarbons, including benzene, toluene, xylene, styrene, biphenyls and cyclohexane. See "Top Value Added Chemicals from Biomass, Volume II: Results of Screening for Potential Candidates from Biorefinery Lignin," October 2007, Pacific Northwest National Laboratory for processes suitable for obtaining phenolic starting materials from lignin, and for additional examples of starting materials.

In some embodiments, the disclosure provides a method for making a functionalized lignin-derived compound that includes converting the phenolic hydroxyl to a leaving group, followed by a coupling reaction to functionalize the monomer at the site at which the phenolic hydroxyl is attached to the aromatic ring. An illustrative coupling reaction utilizes a Grignard reagent in a Kumada coupling. The carbon fragment added to the monomer via Kumada coupling can be selected to add any desired functionality, and can be a carbon chain of any desired length (typically between 1 and 10 carbon atoms, linear to branched), allowing for production of a wider variety of functionalized lignin-derived monomers. Use of the Grignard reaction thus permits greater modularity in monomer design by virtue of selection of the carbon fragment.

Illustrative bifunctional lignin derived monomers disclosed herein include, without limitation, diols, diacids, dialdehydes, diallyls, and diamines, which can contain 0, 1 or 2 methoxy groups depending on the starting material used. Examples of monomers that contain 0 or 1 methoxy groups and alcohol, acid, aldehyde or amine functionalities include, without limitation:

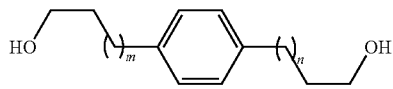

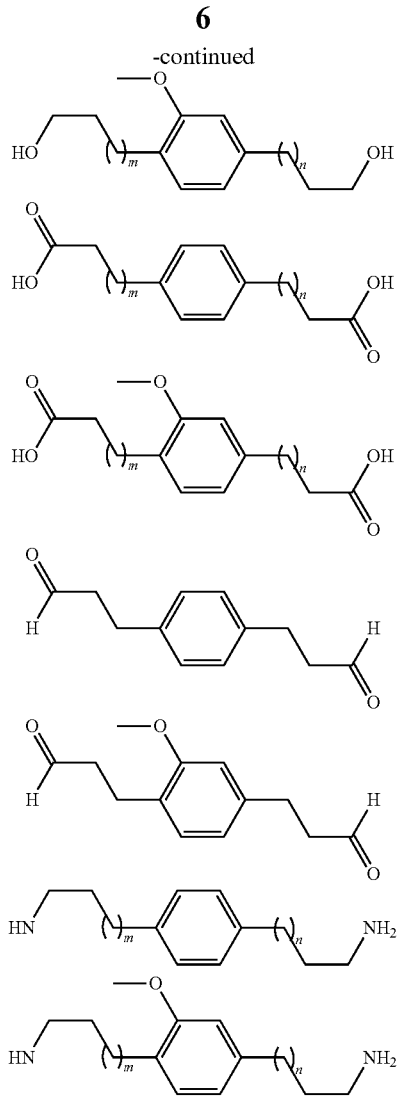

wherein m=0, 1, 2, 3, 4, 5, 6, 7, 8, 9, 10, 11, 12, 13, 14, 15, 16, 17, 18, 19, 20, or more, up to about 50; and n=0, 1, 2, 3, 4, 5, 6, 7, 8, 9, 10, 11, 12, 13, 14, 15, 16, 17, 18, 19, 20, or more, up to about 50; and where m=n or m≠n.

Advantageously, disclosed methods may allow for the ready production of dialdehyde monomers; illustrative chemistries are described in the examples, below. Dialdehydes may be useful intermediates in that they can be readily converted to other functional groups, optionally including the addition of a hydrocarbon extension.

An example of a dialdehyde conversion to a diacid and then to a diol is as follows:

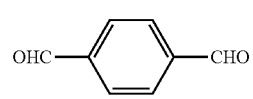

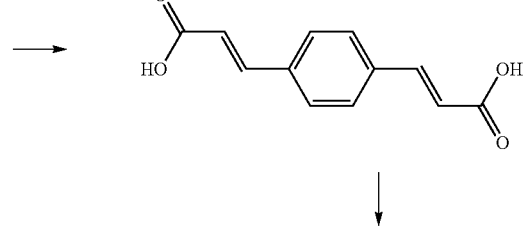

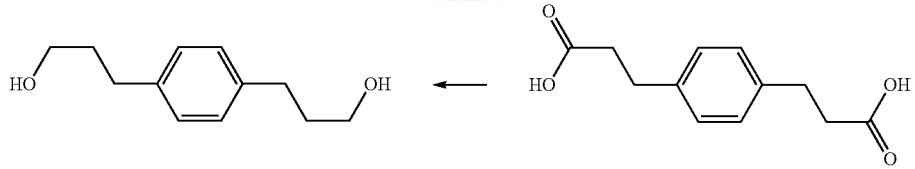

In general, aldehydes can be readily converted to another functional group of interest to form compounds, including for example disclosed compounds.

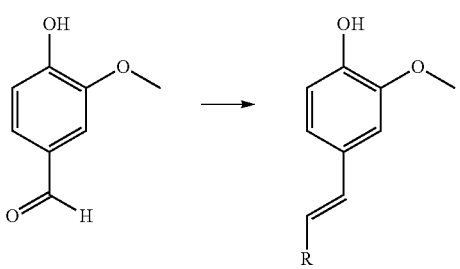

R = Alkyl, aryl, heterocyclic, etc

In some particular examples, compounds of formulae I and IV can be derived from lignins.

Some embodiments include compounds of formula I:

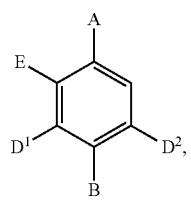

(I)

where

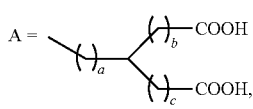

where a is 1, 2 or 3; and b and c are independently 0, 1, 2, or 3; B is A, —OH, or —OR where R is —CH$_3$, —CH$_2$CH$_3$, CH$_2$CH$_2$CH$_3$, CHCH$_2$, CHCHCH$_3$, or CH$_2$CHCH$_2$; D$^1$ and D$^2$ are independently H, —OH, or —OR where R is —CH$_3$, —CH$_2$CH$_3$, CH$_2$CH$_2$CH$_3$, CHCH$_2$, CHCHCH$_3$, or CH$_2$CHCH$_2$; and E is H or together with D$^1$ and the phenyl ring attached thereto forms a naphthalene ring, with the proviso that if a is 1, b is 1, c is 0, D$^2$ is —OCH$_3$, B is —OH, then D$^1$ is not H.

In some illustrative embodiments, both A and B are

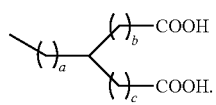

In some illustrative embodiments both A and B have the same structure. In some illustrative embodiments, D$^1$ can be H, or —OH. In some illustrative embodiments, D$^1$ can be H. In some illustrative embodiments, D$^1$ together with E and the phenyl ring attached thereto form a naphthalene ring.

In some illustrative embodiments, compounds of formula I can include, for example

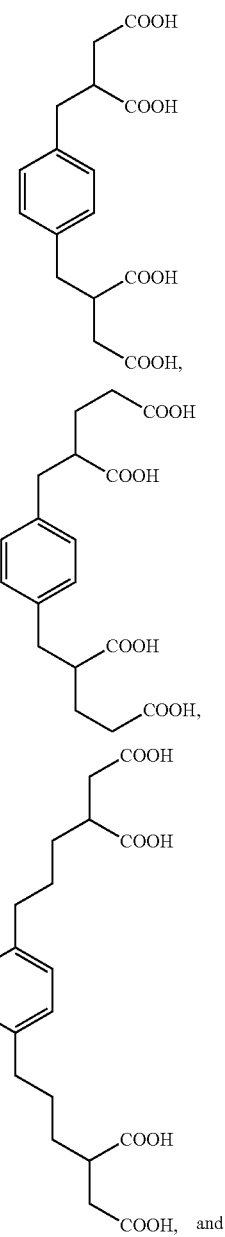

and

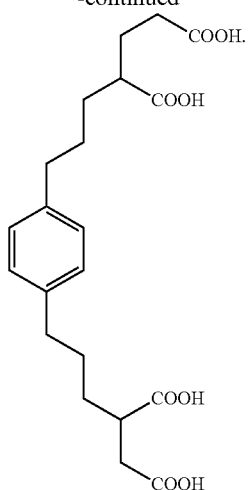
While in some illustrative embodiments, compounds of formula I can include, for example
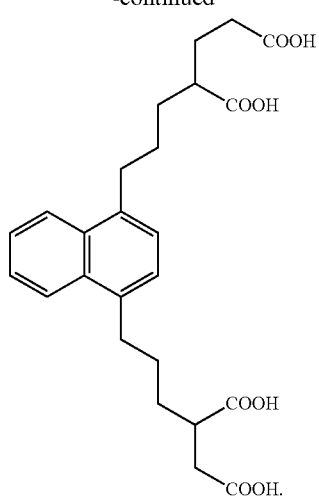
While in some other illustrative embodiments, compounds of formula I can include, for example
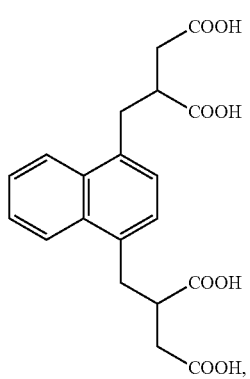
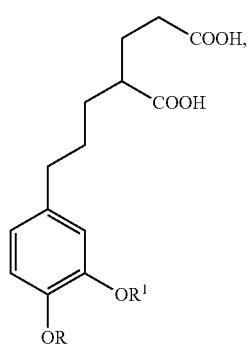
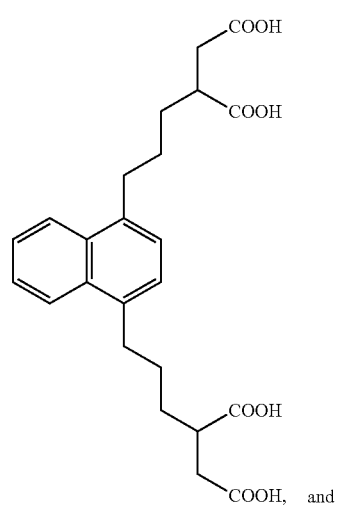
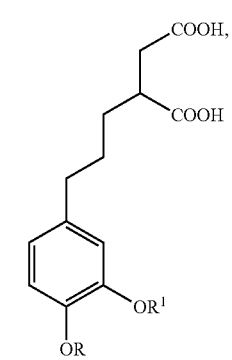
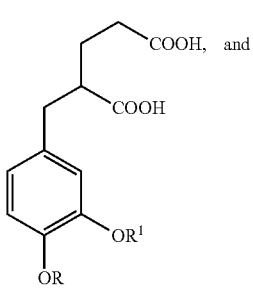

-continued

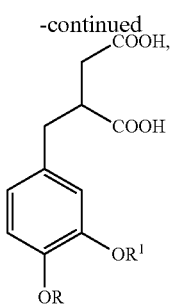

where R is as defined above and R¹ can be —$CH_3$, —$CH_2CH_3$, $CH_2CH_2CH_3$, $CHCH_2$, $CHCHCH_3$, or $CH_2CHCH_2$.

In some embodiments, formula I does not include a compound of the following formula:

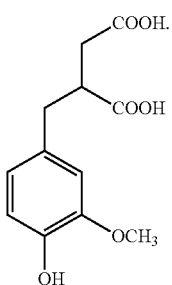 [SMILES: COc1cc(CC(CC(=O)O)C(=O)O)ccc1O]

In some embodiments, compounds of formula I can be derived from lignins. In some embodiments, compounds of formula I can be derived from lignins that are depolymerized. In some such embodiments, depolymerized lignins include phenolic hydroxyl groups, which can be converted to leaving groups. In some embodiments depolymerized lignins can be modified by extending the carbon chain, for example using Kumada coupling. In some embodiments, compounds of formula I can be derived from eugenol, isoeugenol, guiacol, vanillin, isovanillin, chavicol, chavibetol, or combinations thereof.

In some embodiments, compounds of formula I can be polymerized, either with or without other components. In some embodiments polymerization of compounds of formula I can be accomplished using free radical polymerization. In some embodiments, polymerized compounds of formula I can be nylons, polyesters, polyurethanes, polyamides, or combinations thereof. In some embodiments polymerized compounds according to formula I can be used as an adhesive, a plastic, a thermoplastic, a gel, a coating, a film, or any combination thereof.

Some embodiments include compounds of formula IV:

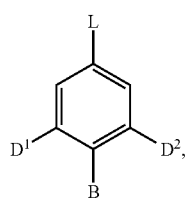

(IV)

where L is —$(CH_2)_h$COOH, where h is 4, 5, or 6,
B is —OH, or —OR where R is —$CH_3$, —$CH_2CH_3$, $CH_2CH_2CH_3$, $CHCH_2$, $CHCHCH_3$, or $CH_2CHCH_2$;
D¹ and D² are independently H, —OH, or —OR where R is —$CH_3$, —$CH_2CH_3$, $CH_2CH_2CH_3$, $CHCH_2$, $CHCHCH_3$, or $CH_2CHCH_2$.

In some illustrative embodiments, D¹ can be H, or —OH.
In some illustrative embodiments, D¹ can be H.
In some illustrative embodiments, compounds of formula IV can include, for example

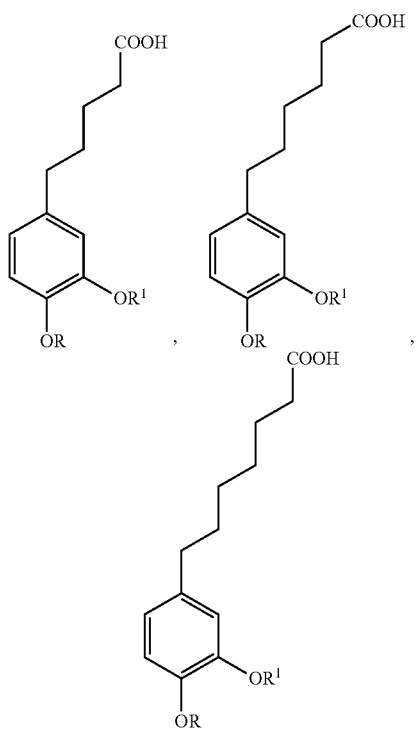

where both R and R¹ can be —$CH_3$, —$CH_2CH_3$, $CH_2CH_2CH_3$, $CHCH_2$, $CHCHCH_3$, or $CH_2CHCH_2$.

In some embodiments, compounds of formula IV can be derived from lignins. In some embodiments, compounds of formula IV can be derived from lignins that are depolymerized. In some such embodiments, depolymerized lignins include phenolic hydroxyl groups, which can be converted to leaving groups. In some embodiments depolymerized lignins can be modified by extending the carbon chain, for example using Kumada coupling. In some embodiments, compounds of formula IV can be derived from eugenol, isoeugenol, guiacol, vanillin, isovanillin, chavicol, chavibetol, or combinations thereof.

In some embodiments, compounds of formula IV can be polymerized, either with or without other components. In some embodiments polymerization of compounds of formula IV can be accomplished using free radical polymerization. In some embodiments, polymerized compounds of formula IV can be nylons, polyesters, polyurethanes, polyamides, or combinations thereof. In some embodiments polymerized compounds according to formula IV can be used as an adhesive, a plastic, a thermoplastic, a gel, a coating, a film, or any combination thereof.

In some embodiments, disclosed compounds can include illustrative structures and/or compounds seen in compounds 1 to 13 below, which may be derived using disclosed methods or other methods, for example, from lignin compounds.

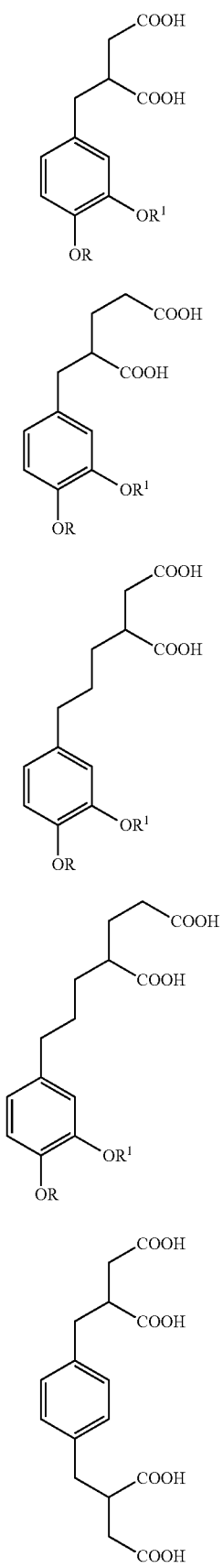
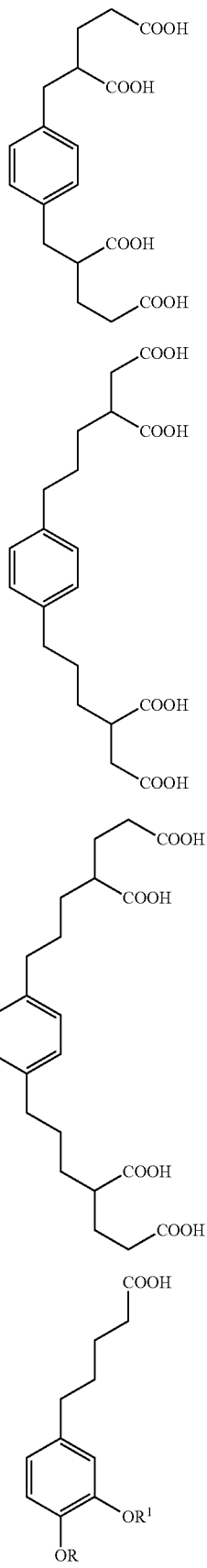

(Cmpd. 10)

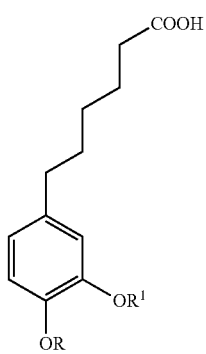

(Cmpd. 11)

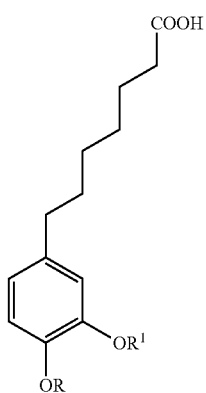

(Cmpd. 12)

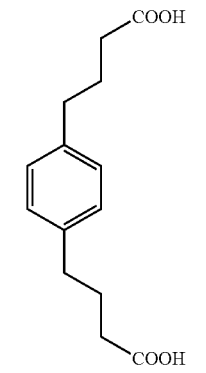

(Cmpd. 13)

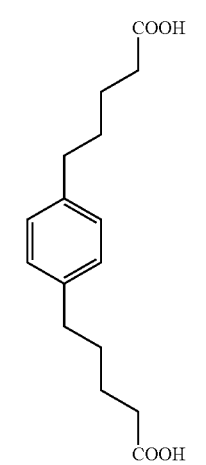

In some embodiments, disclosed compounds can include illustrative structures seen in compounds 14 to 16 below, which may be derived using disclosed methods or other methods, for example, from lignin compounds.

(Cmpd. 14)

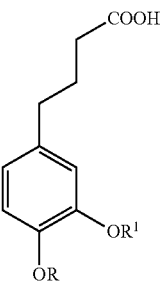

(Cmpd. 15)

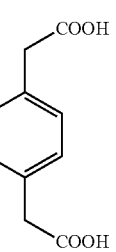

(Cmpd. 16)

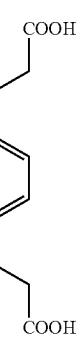

Cellulose

Disclosed herein are compounds that are specifically obtained from cellulose.

With respect to biomass derived from cellulose and hemicellulose, the present disclosure provides methods for the conversion of fructose, which is readily available from cellulose by degradation and isomerization, to a wide variety of monomers for polymer synthesis with novel properties. 5-Hydroxymethylfurfural (HMF) is a primary product of fructose dehydration and can serve as the starting material for the preparation of many of the furan-based compounds described herein. HMF can be converted to other important intermediates, such as 2,5-furandicarboxylic acid (FDCA), 2,5-diformylfuran, and 2,5-furylbis(propenoic acid), which can be utilized directly or can serve as further intermediates for the synthesis of additional monomers with the potential utility to replace terephthalic acid and other petroleum-derived monomers.

Examples of monomers that can be derived from HMF according to the current disclosure include those seen below:

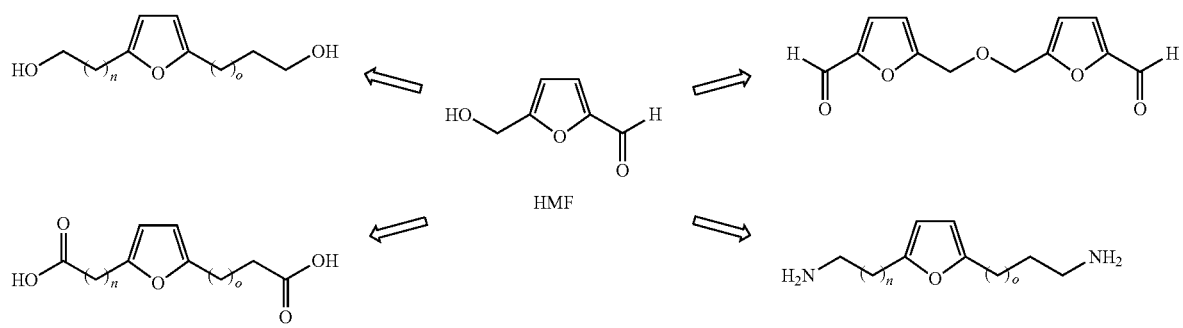

where n and o are independently selected from 0, 1, 2, 3, 4, 5, 6, 7, 8, 9, 10, up to 20, up to 30, up to 40 up to 50, or even higher.

Additionally, HMF and its 2,5-substituted derivatives can be reacted in a Diels-Alder reaction, followed by a deoxygenation/aromatization step to yield bicyclic naphthalene derivatives. A wide variety of symmetric and asymmetric naphthalene derivatives can be generated, since variation is introduced via the particular HMF derivative selected as a starting material.

Examples of naphthalene containing compounds that are disclosed herein and that can be derived from HMF or its derivatives include:

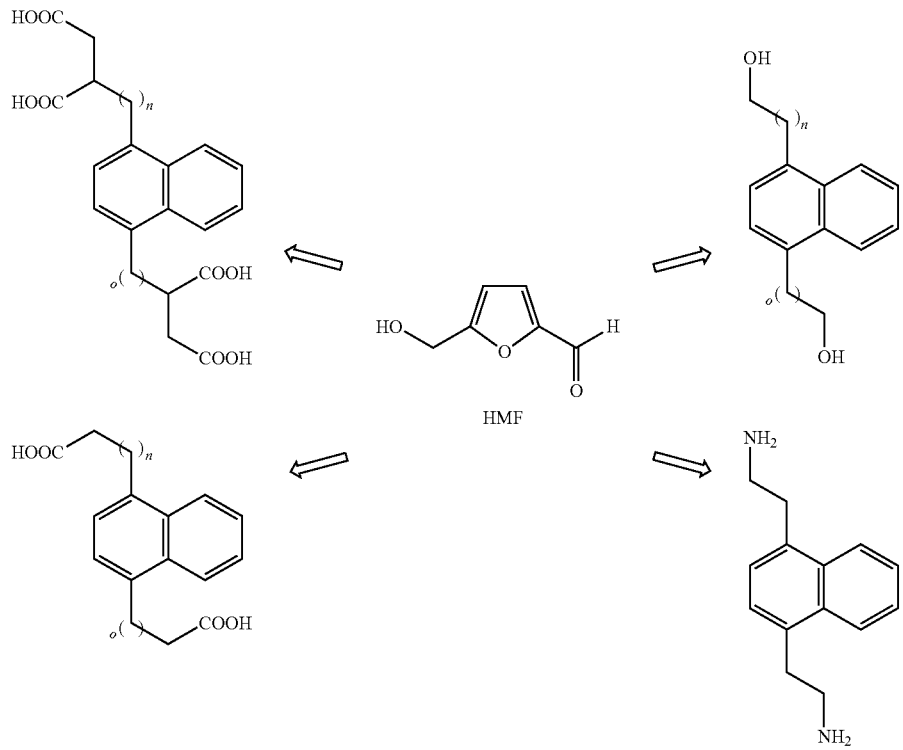

where n and o are independently selected from 0, 1, 2, 3, 4, 5, 6, 7, 8, 9, 10, up to 20, up to 30, up to 40 up to 50, or even higher.

Dimers of HMF and its 2,5-substituted derivatives, formed via condensation, can also serve as starting materials.

Examples of disclosed compounds that may be derived from dimers of HMF or its derivatives include:

where n and o are independently selected from 0, 1, 2, 3, 4, 5, 6, 7, 8, 9, 10, up to 20, up to 30, up to 40 up to 50, or even higher.

Compounds of formulae II, III, and V can be derived from cellulose, hemicellulose, or combinations thereof, through HMF, for example.

Some embodiments include compounds of formula II:

(II)

where $G^1$ and $G^2$ are independently where a is 1, 2 or 3; and b and c are independently 0, 1, 2, or 3,
$(CH_2)_d OH$ where d is 1, 2, 3, 4 or 5, or
—$(CH_2)_e COOH$ where e is 0, 1, 2, 3, 4 or 5,
with the caveat that if both $G^1$ and $G^2$ are —$(CH_2)_e COOH$ and one of e is 2 then the other e is not 0 or 2.

In some illustrative embodiments, compounds of formula II include those in which both $G^1$ and $G^2$ are In some such illustrative embodiments, compounds of formula II include those in which at least one of b and c in both $G^1$ and $G^2$ are 0. In some such illustrative embodiments, compounds of formula II include those in which only one of b and c in both $G^1$ and $G^2$ are 0. In some such illustrative embodiments, compounds of formula II include those in which the structure of $G^1$ and $G^2$ are the same.

In some illustrative embodiments, compounds of formula II can include, for example In some illustrative embodiments, compounds of formula II include those in which one of $G^1$ and $G^2$ is —$(CH_2)_d OH$. In some such illustrative embodiments, compounds of formula II include those in which the other of $G^1$ and $G^2$ is In some illustrative embodiments, compounds of formula II can include, for example

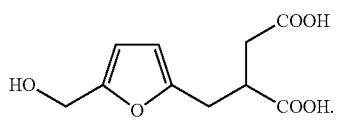

In some illustrative embodiments, compounds of formula II include those in which both $G^1$ and $G^2$ are $-(CH_2)_e$ COOH. In some illustrative embodiments, compounds of formula II can include, for example

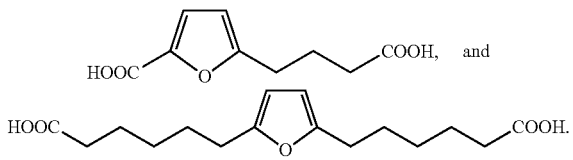

In some embodiments, compounds of formula II can be derived from cellulose, hemicellulose, or combinations thereof. In some embodiments, compounds of formula II can be derived from fructose from cellulose, hemicellulose or a combination thereof. In some such embodiments, the fructose can be dehydrated to form 5-hydroxymethylfurfural (HMF).

In some embodiments, compounds of formula II can be polymerized, either with or without other components. In some embodiments polymerization of compounds of formula II can be accomplished using free radical polymerization. In some embodiments, polymerized compounds of formula II can be nylons, polyesters, polyurethanes, polyamides, or combinations thereof. In some embodiments polymerized compounds according to formula II can be used as an adhesive, a plastic, a thermoplastic, a gel, a coating, a film, or any combination thereof.

Some embodiments include compounds of formula III:

$$HOOC(CH_2)_f\text{-}J\text{-}(CH_2)_g COOH \qquad (III),$$

where J is selected from:

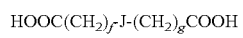

and f is 3, 4 or 5 and g is 0, 3, 4 or 5.

In some illustrative embodiments, compounds of formula III can include those in which J

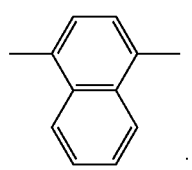

In some such illustrative embodiments, compounds of formula III can include those in which f and g are the same.

In some illustrative embodiments, compounds of formula III can include, for example

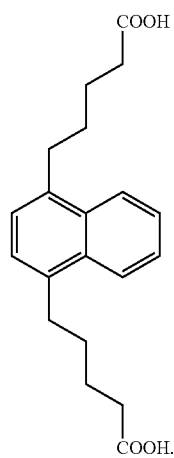 [SMILES: O=C(O)CCCCc1ccc(CCCCC(=O)O)c2ccccc12]

In some illustrative embodiments, compounds of formula III can include those in which J is

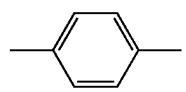

In some such illustrative embodiments, compounds of formula III can include those in which f and g are the same. In some such illustrative embodiments, compounds of formula III can include those in which f and g are 3 or 4.

In some illustrative embodiments, compounds of formula III can include, for example

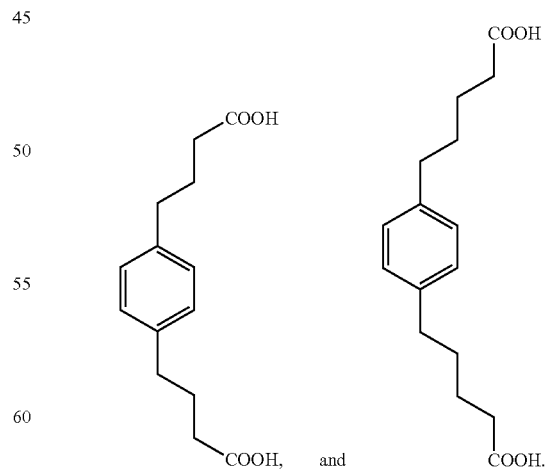

In some illustrative embodiments, compounds of formula III can include those in which J is

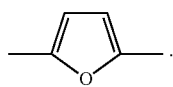

In some such illustrative embodiments, compounds of formula III can include those in which f and g are the same. In some illustrative embodiments, compounds of formula II can include, for example

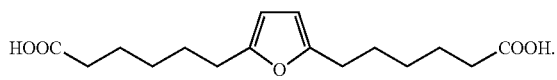 [SMILES: O=C(O)CCCCCc1ccc(CCCCCC(=O)O)o1]

In some such illustrative embodiments, compounds of formula III can include those in which f and g are not the same. In some illustrative embodiments, compounds of formula II can include, for example

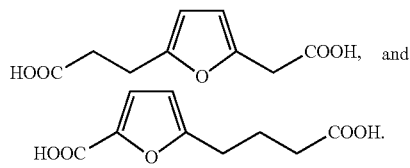

In some embodiments, compounds of formula III can be derived from cellulose, hemicellulose, or combinations thereof. In some embodiments, compounds of formula III can be derived from fructose from cellulose, hemicellulose or a combination thereof. In some such embodiments, the fructose can be dehydrated to form 5-hydroxymethylfurfural (HMF).

In some embodiments, compounds of formula III can be polymerized, either with or without other components. In some embodiments polymerization of compounds of formula III can be accomplished using free radical polymerization. In some embodiments, polymerized compounds of formula III can be nylons, polyesters, polyurethanes, polyamides, or combinations thereof. In some embodiments polymerized compounds according to formula III can be used as an adhesive, a plastic, a thermoplastic, a gel, a coating, a film, or any combination thereof.

Some embodiments include compounds of formula V:

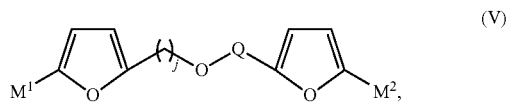
(V)

where $M^1$ and $M^2$ are independently $—(CH_2)_k OH$ where k is 2, 3, or 4, $—(CH_2)_m O(CH_2)_n NH_2$ where m an n are integers from 1 to 10; j is 1, 2, or 3; and Q is $—(CH_2)_p$ where p is 1, 2 or 3, or $—(CH_2)_q O(CH_2)_r$ where q and r are independently an integer from 1 to 10.

In some illustrative embodiments, compounds of formula V can include those in which $M^1$ and $M^2$ are both $—(CH_2)_k OH$. In some illustrative embodiments, compounds of formula V can include those in which $M^1$ and $M^2$ are the same. In some illustrative embodiments, compounds of formula V can include, for example

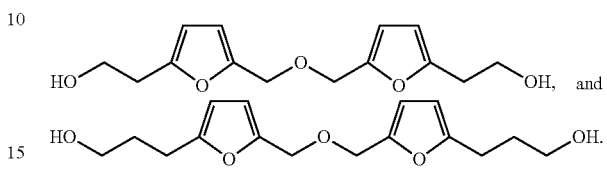

In some illustrative embodiments, compounds of formula V can include those in which Q is $—(CH_2)_q O(CH_2)_r$. In some illustrative embodiments, compounds of formula V can include, for example

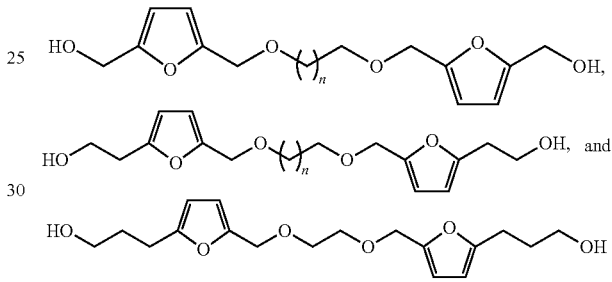

where n is an integer from 1 to 10.

In some illustrative embodiments, compounds of formula V can include those in which $M^1$ and $M^2$ are both $—(CH_2)_m O(CH_2)_n NH_2$. In some illustrative embodiments, compounds of formula V can include, for example

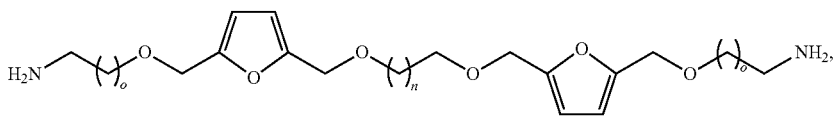

where o and n are integers from 1 to 10.

In some embodiments, compounds of formula V can be derived from cellulose, hemicellulose, or combinations thereof. In some embodiments, compounds of formula V can be derived from fructose from cellulose, hemicellulose or a combination thereof. In some such embodiments, the fructose can be dehydrated to form 5-hydroxymethylfurfural (HMF).

In some embodiments, compounds of formula V can be polymerized, either with or without other components. In some embodiments polymerization of compounds of formula V can be accomplished using free radical polymerization. In some embodiments, polymerized compounds of formula V can be nylons, polyesters, polyurethanes, polyamides, or combinations thereof. In some embodiments polymerized compounds according to formula V can be used as an adhesive, a plastic, a thermoplastic, a gel, a coating, a film, or any combination thereof.

In some embodiments, disclosed compounds can include illustrative structures and/or compounds seen in compounds 17 to 20 below, which include a naphthalene group, which may be derived using disclosed methods, for example, from cellulose compounds.

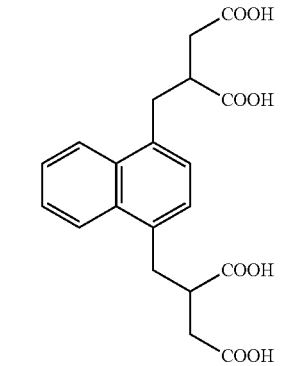
(Cmpd. 17)

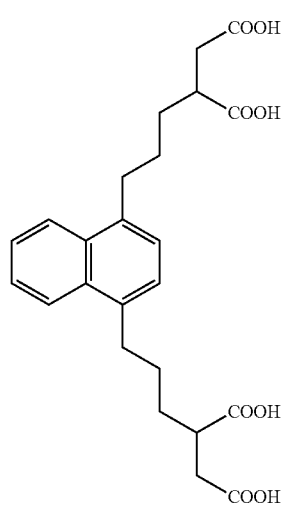
(Cmpd. 18)

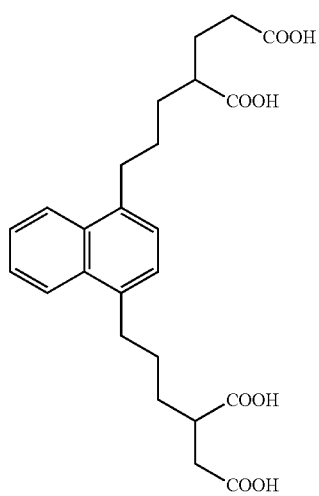
(Cmpd. 19)

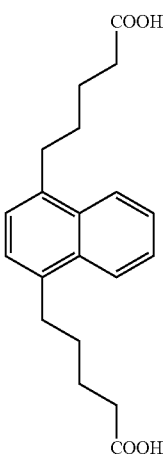
(Cmpd. 20)

In some embodiments, disclosed compounds can include illustrative structures and/or compounds seen in compounds 21 to 23 below, which include a naphthalene group, which may be derived using disclosed methods, for example, from cellulose compounds.

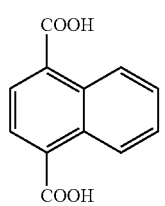
(Cmpd. 21)

(Cmpd. 22)

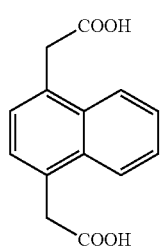
(Cmpd. 23)

In some embodiments, disclosed compounds can include illustrative structures and/or compounds seen in compounds 24 to 29 below, which include a furan group, which may be derived using disclosed methods, for example, from cellulose compounds.

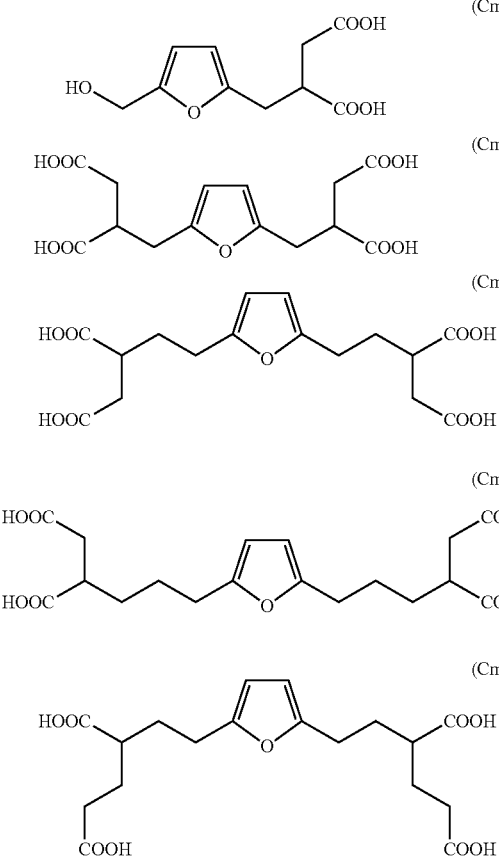

(Cmpd. 24)
(Cmpd. 25)
(Cmpd. 26)
(Cmpd. 27)
(Cmpd. 28)

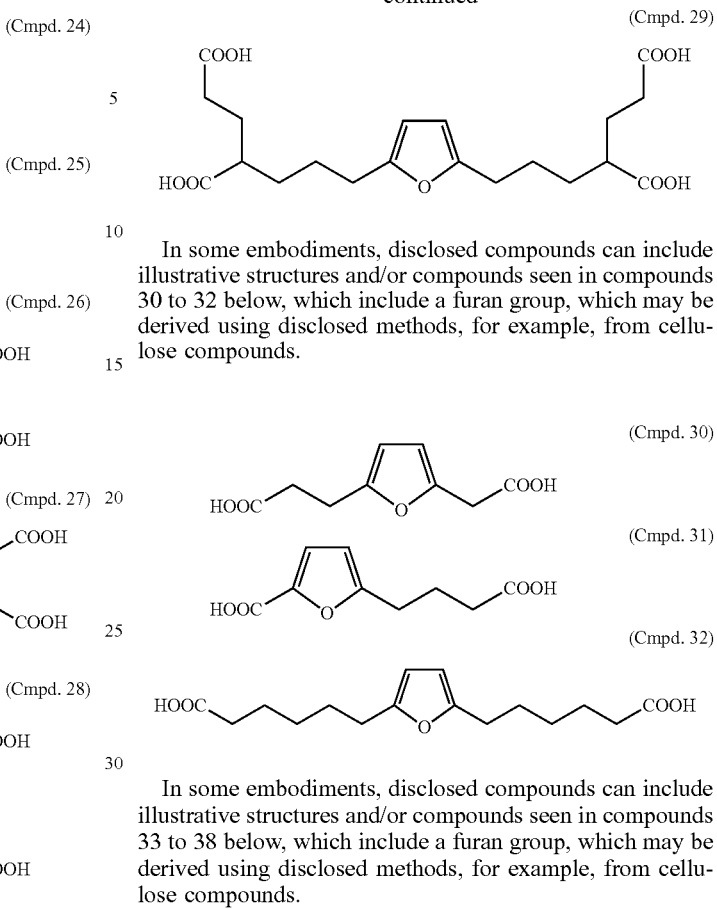

(Cmpd. 29)

In some embodiments, disclosed compounds can include illustrative structures and/or compounds seen in compounds 30 to 32 below, which include a furan group, which may be derived using disclosed methods, for example, from cellulose compounds.

(Cmpd. 30)
(Cmpd. 31)
(Cmpd. 32)

In some embodiments, disclosed compounds can include illustrative structures and/or compounds seen in compounds 33 to 38 below, which include a furan group, which may be derived using disclosed methods, for example, from cellulose compounds.

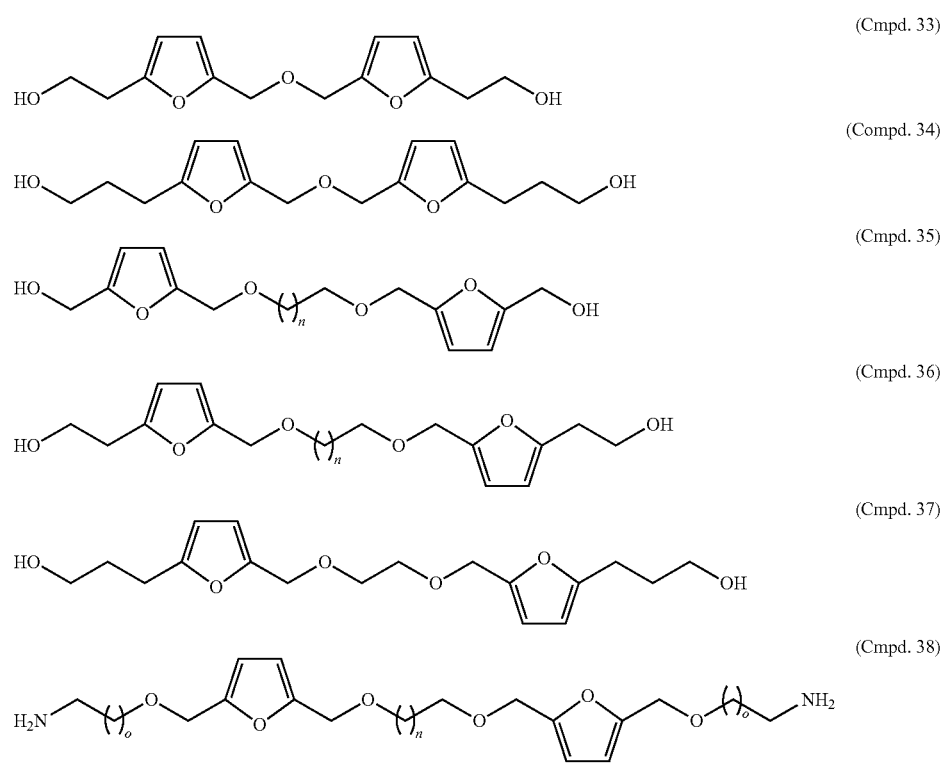

(Cmpd. 33)
(Compd. 34)
(Cmpd. 35)
(Cmpd. 36)
(Cmpd. 37)
(Cmpd. 38)

In some embodiments, disclosed compounds can include illustrative structures and/or compounds seen in compounds 39 to 42 below, which include a furan group, which may be derived using disclosed methods, for example, from cellulose compounds.

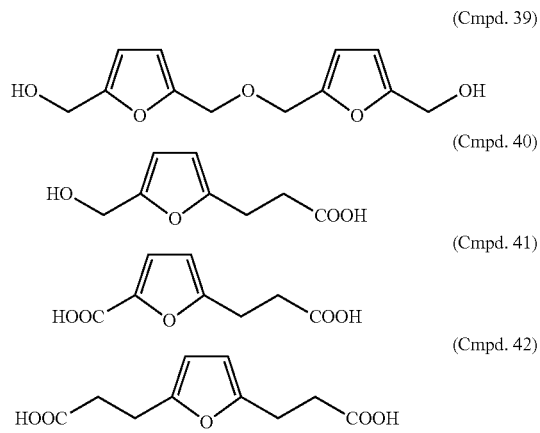

(Cmpd. 39)
(Cmpd. 40)
(Cmpd. 41)
(Cmpd. 42)

The compounds, or monomers disclosed herein are typically functionalized, and can be optionally polyfunctionalized. The term "polyfunctionalized" includes functionalization with two (bifunctionalization) or more functional groups, which can be the same or different. Functionalization includes, but is not limited to, incorporation of a hydroxyl, aldehyde, carboxylic acid, amine, amide, ester, vinyl or allyl group into the monomer. Polyfunctionalized monomers can be symmetric or asymmetric. Monomers incorporating one or more aldehyde, carboxylic acid, amine, or alcohol are especially useful as they can generally be interconverted, as well as extended by the addition of carbon fragments, using standard chemistries.

The present disclosure encompasses not only synthetic methods, but also the compounds, e.g., monomers as described herein, which are expected to be useful substitutes for petroleum based-monomers in commercial and industrial polymers. For example, the disclosure provides for the synthesis of novel terephthalic acid analogs from monomers derived from biomass, thereby providing bio-based or "green" monomers that can be substituted for terephthalic acid and its derivatives in industrial polymers and copolymers. The monomers of this disclosure have high market value as commodity and specialty chemicals, green building materials, nylons, resins, and plastics Exemplary monomers derived from lignin and cellulosic biomass include, without limitation:

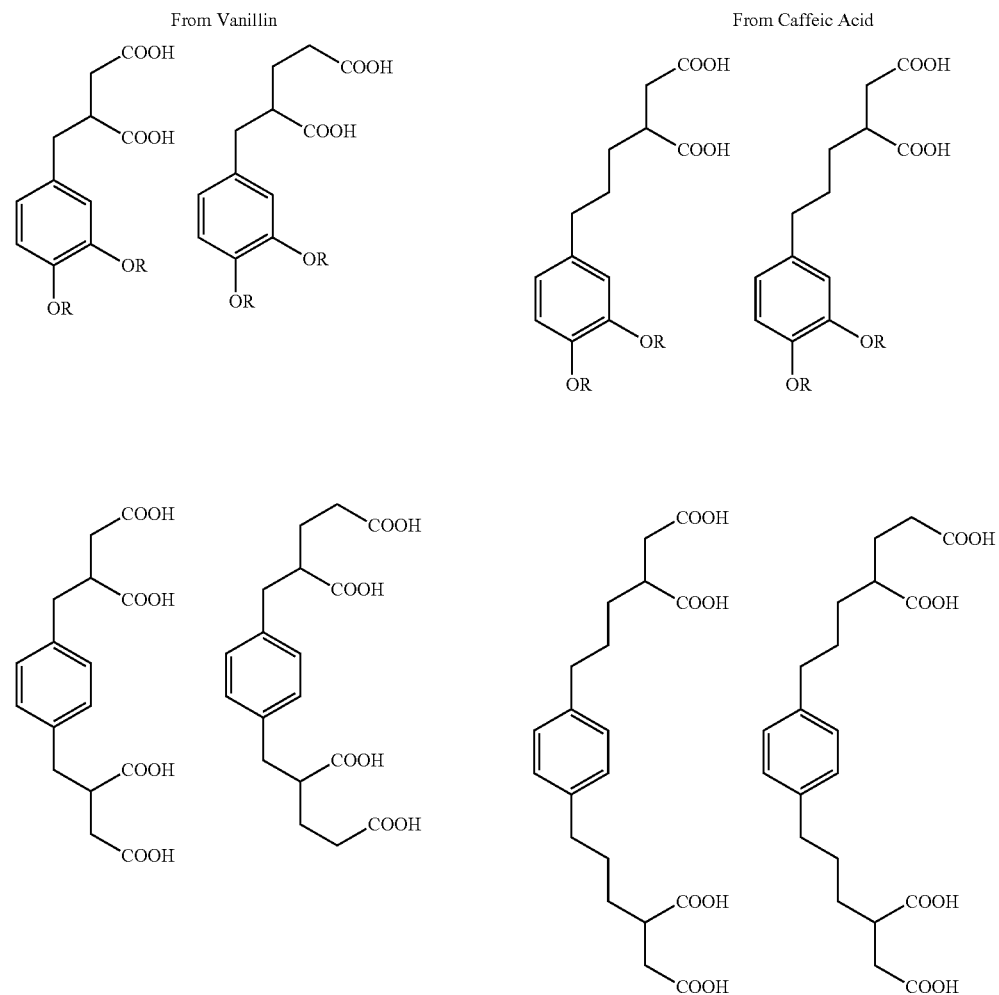

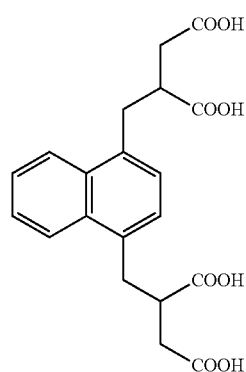
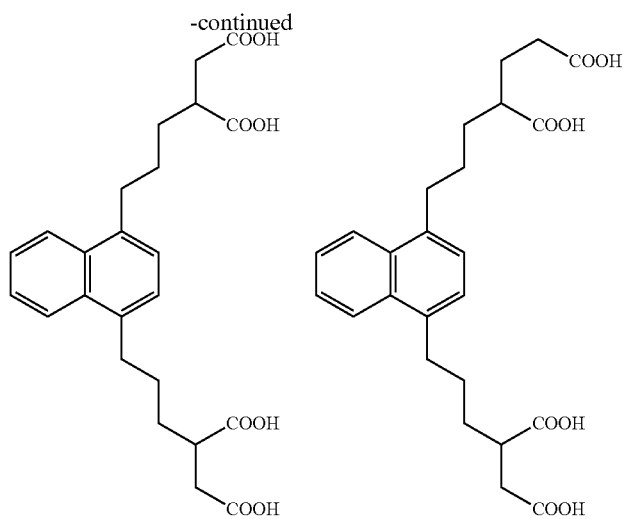
Carboxylic Acids from HMF
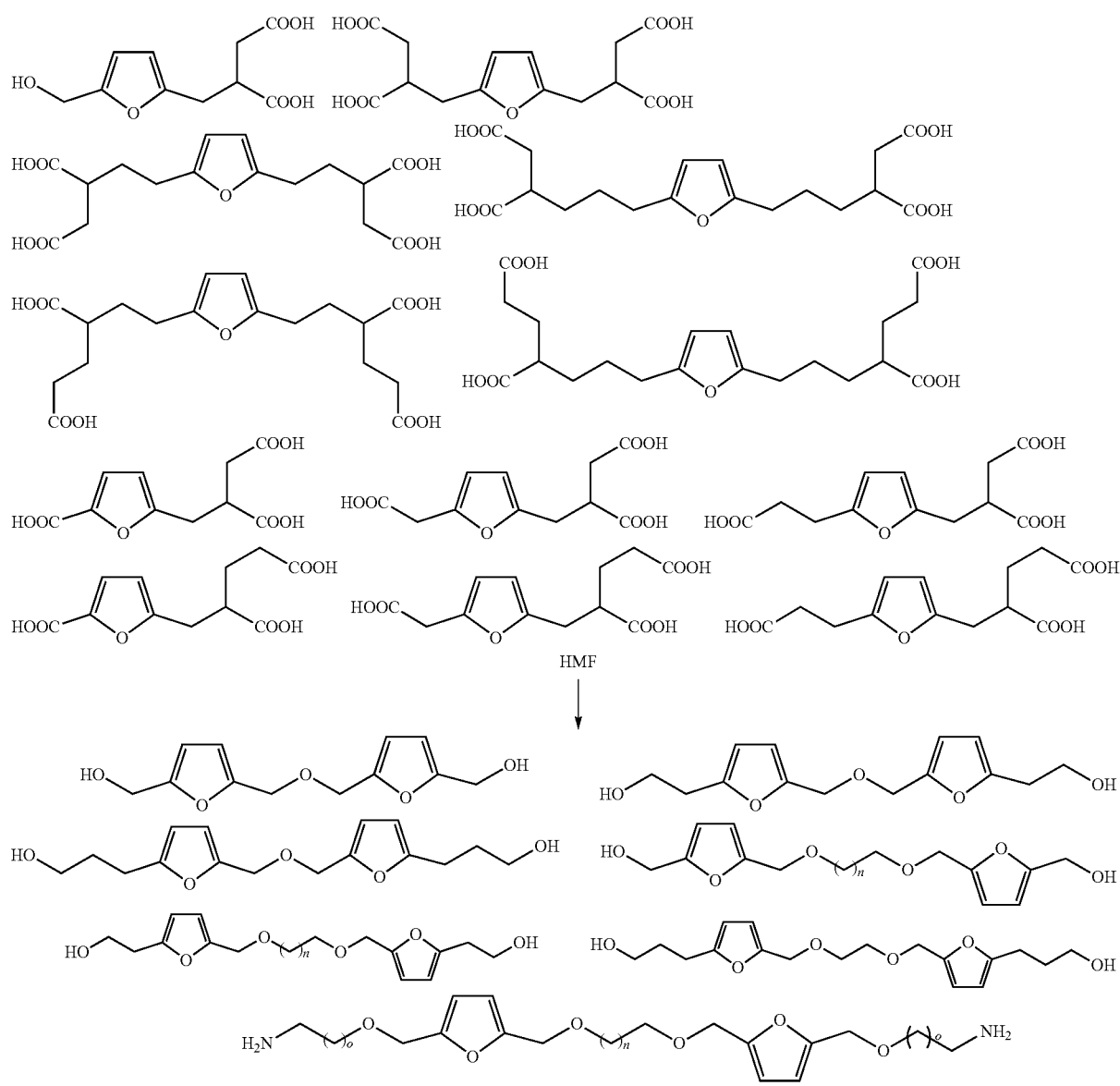
HMF
We can also make polyesters, polyamides, urethanes, etc.

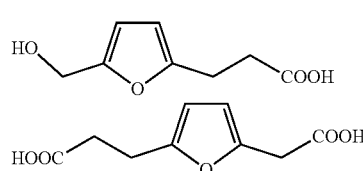
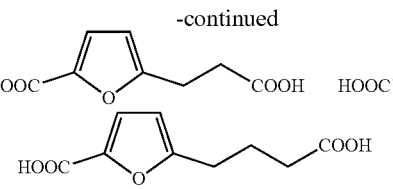
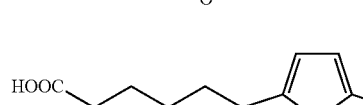
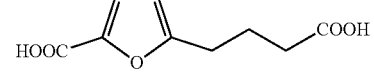
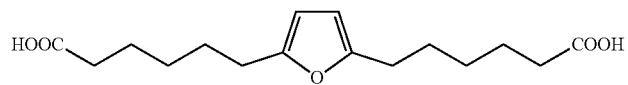
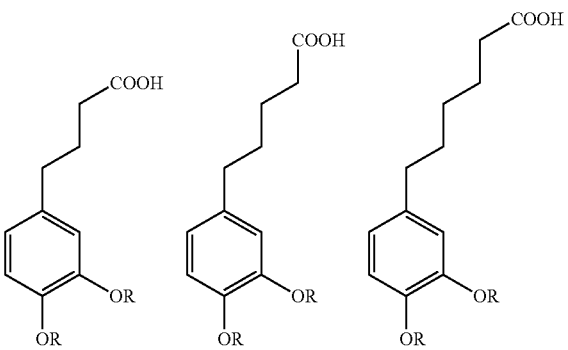
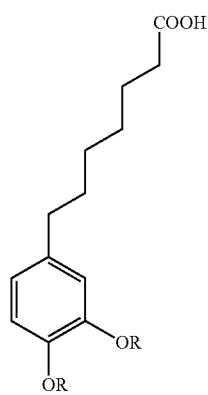
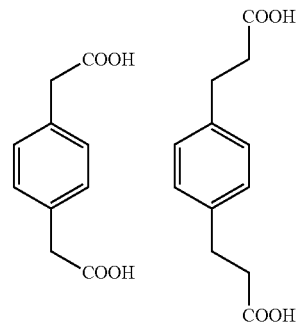
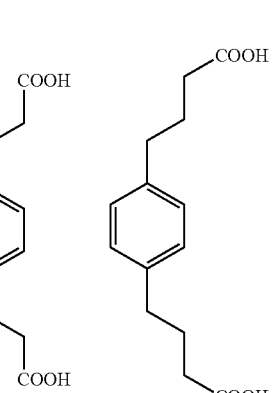
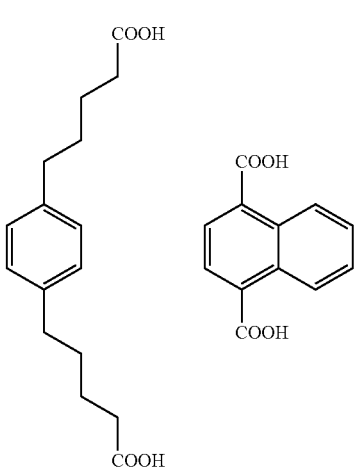
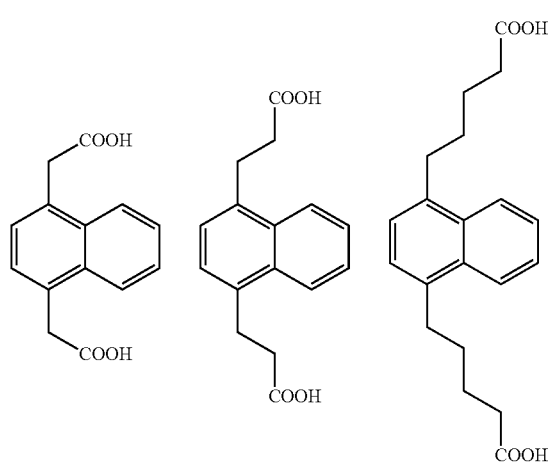

It is expected that the monomers disclosed herein can be readily incorporated into polymers and copolymers including nylons, polyesters, polyurethanes, polyamides and the like. This disclosure thus further includes methods for utilizing the novel bio-based monomer in any polymerization reaction including, but not limited to, free radical polymerization, as well as the resulting polymers. Polymers incorporating the novel bio-based monomer can be homopolymers or copolymers. The term "copolymer" includes, without limitation, alternating or periodic copolymers, statistical or random copolymers, terpolymers, star polymers, block copolymers such as diblock or tri block copolymers, and graft copolymers. A copolymer may be linear or branched. The disclosure thus also encompasses polymers and copolymers comprising the novel monomers disclosed herein, as well as polymeric compositions such as adhesives, plastics, thermoplastics, gels, coatings and films. Articles including the novel polymers and copolymers, for example plastic beverage bottles, are also encompassed by this disclosure.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

For hydrocarbon chain lengths designated by a variable such as "m", "n", or "o", m, n, and/or o are independently selected from 0, 1, 2, 3, 4, 5, 6, 7, 8, 9, 10, up to 20, up to 30, up to 40 up to 50, or even higher.

The examples that follow more particularly exemplify illustrative embodiments. In several places throughout the application, guidance is provided through lists of examples, which examples can be used in various combinations. In each instance, the recited list serves only as a representative group and should not be interpreted as an exclusive list.

EXAMPLES

The present disclosure is illustrated by the following examples. It is to be understood that the particular examples, materials, amounts, and procedures are to be interpreted broadly in accordance with the scope and spirit of the invention as set forth herein.

Example I

Synthesis of Furan Monomers from 5-Hydroxymethylfurfural (HMF)

The present invention allows fructose, which is readily available from cellulose by degradation and isomerization, to be converted to a wide variety of monomers for polymer synthesis with novel properties. 5-Hydroxymethylfurfural (HMF, 1) is a primary product of fructose dehydration and serves as the starting material for the preparation of many of the furan-based compounds described herein. HMF can be oxidized to 2,5-furandicarboxylic acid (FDCA, 2) which is another important starting material for preparation of many of the furan-based compounds described herein. Advantageously, HMF can be converted into a number of compounds such as FDCA, 2,5-diformylfuran, and 2,5-furylbis (propenoic acid) which can be utilized directly or can serve as intermediates for the synthesis of additional monomers with the potential utility to replace terephthalic acid.

The illustrative scheme below shows the general steps for obtaining HMF and its oxidized derivative FDCA from cellulose, and lists a variety of furan-based monomers that can be obtained using HMF as a starting material. Details of exemplary procedures for the synthesis of a variety of furan-based monomers are provided.

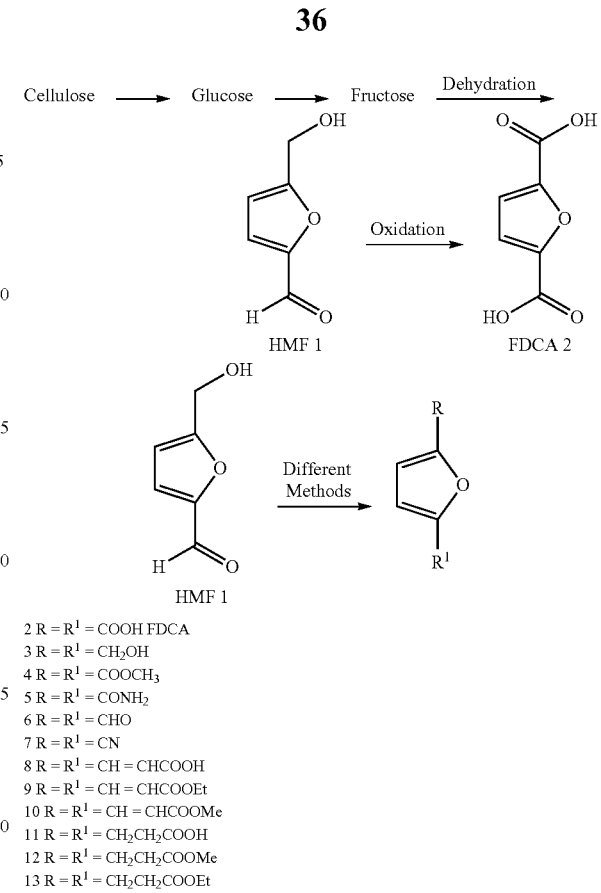

2 R = R$^1$ = COOH FDCA
3 R = R$^1$ = CH$_2$OH
4 R = R$^1$ = COOCH$_3$
5 R = R$^1$ = CONH$_2$
6 R = R$^1$ = CHO
7 R = R$^1$ = CN
8 R = R$^1$ = CH = CHCOOH
9 R = R$^1$ = CH = CHCOOEt
10 R = R$^1$ = CH = CHCOOMe
11 R = R$^1$ = CH$_2$CH$_2$COOH
12 R = R$^1$ = CH$_2$CH$_2$COOMe
13 R = R$^1$ = CH$_2$CH$_2$COOEt

A. Synthesis of 5-Hydroxymethylfurfural 1 (HMF) from Fructose

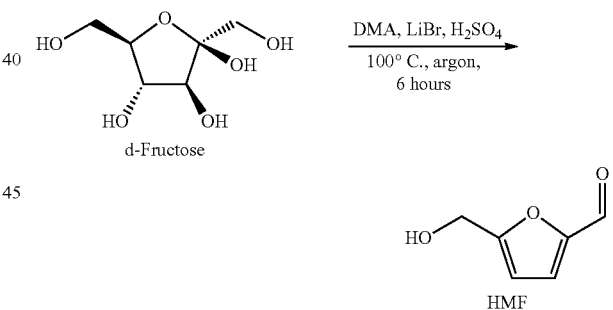

Reaction Scheme for the Synthesis of HMF from Fructose

A modified literature procedure was adopted (Binder et al., J. Am. Chem. Soc. 2009 131, 1979). To an oven dried 250 mL 2-neck RB fitted with a condenser, D-fructose (10 g, 55.5 mmol) and N,N-dimethylacetamide (DMAc, 100 mL) were added under a nitrogen atmosphere. To this, LiBr (10 g) was added, followed by catalytic amount of H$_2$SO$_4$ (0.326 g, 3.33 mmol, 0.06 equiv. 0.17 mL) and stirred at 100° C. for 6 h. After completion, the reaction mixture was cooled to room temperature and filtered through a bed of Celite to remove the insolubles. The Celite bed was washed with ethyl acetate (3×25 mL). The Ethyl acetate in the filtrate was removed under reduced pressure followed by DMAc using vacuum distillation. The residue left after vacuum distillation was diluted with ethyl acetate, washed with saturated brine solution, dried over Na$_2$SO$_4$ and the solvent removed under vacuum. Pure compound was obtained by column chromatography using hexane-ethyl acetate (60:40) as an eluent and silica gel (300-400 Mesh) as a stationary phase. 5-hydroxymethylfurfural was obtained as a pale yellow viscous liquid (which solidifies upon cooling) in 3.17 g (45% yield). $^1$H NMR (400 MHz, CDCl$_3$) δ: 9.53 (s, 1H), 7.19 (d, 1H, J=3.5 Hz), 6.49 (d, 1H, J=3.5 Hz), 4.68 (s, 2H), 3.27 (s (broad), 1H).

B. Synthesis of 2,5-Furandicarboxylic Acid 2 (FDCA)

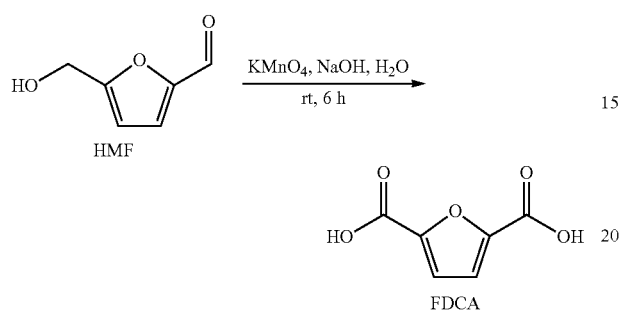

Reaction Scheme for the Synthesis of FDCA from HMF

A modified literature procedure was adopted (US Pat. Publ. US 2007232815, Oct. 4, 2007). To a solution of HMF (6.99 g, 55.5 mmol) in H$_2$O (370 mL), aq. NaOH (51 g, 12.8 mol in 93 mL of H$_2$O) was added and then KMnO$_4$ (0.127 mmol) was added and the reaction mixture was stirred at room temperature for 3-12 h. After completion, the reaction mixture was filtered to remove the insolubles and the filtrate was subsequently cooled to 0-5° C. with ice. After cooling, pH of the solution was adjusted to ~1 with concentrated HCl, during which a pale yellow precipitate was formed. The precipitate was isolated by filtration, washed with excess water and dried in a high vacuum at 60° C. to give a pale yellow solid in 5.04 g (64% yield). $^1$H NMR (500 MHz, DMSO-d$_6$) δ: 7.28 (s, 2H); HRMS [ESI-MS] m/z: Calculated for C$_6$H$_3$O$_4$Na [M-OH] 139.0026 found 139.0018.

C. Synthesis of Dimethyl-2,5-Furandicarboxylate 4

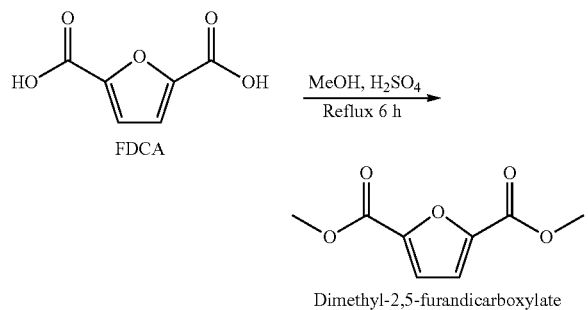

Reaction Scheme for the Synthesis of Dimethyl-2,5-Furandicarboxylate from FDCA

To a 500 mL single necked round bottomed flask (24/40) was added a large PTFE coated magnetic spinning egg, 2,5-furandicarboxylic acid, FDCA (2.9 g, 19 mmol), HPLC grade methanol (200 mL) and concentrated sulfuric acid (0.5 mL). The flask was fitted with a Dimroth condenser (plumbed with 18° C. water flow) and sealed with a red rubber serum septum. The system was flushed with dry nitrogen and heated to a healthy reflux with a Glass-Cool heating mantle/Variac under positive nitrogen pressure. Following six hours of reflux, thin layer chromatography indicated that the reaction was complete. The mixture was concentrated by rotary evaporation to a small volume (it became laden with crystalline precipitate) and was diluted with water. The mixture was chilled on ice and the solid precipitate was isolated by suction filtration. The filter-cake was pressed dry and the residue was chopped and spread on paper to air dry. The dry Dimethyl-2,5-furandicarboxylate (3.2 g, 17 mmol, 89% yield) was a cream colored solid.

$^1$H NMR (CDCl$_3$, 400 MHz) δ: 3.59 (s, 6H), 7.23 (d, 2H)

D. Synthesis of 2,5-Furandicarboxamide 5

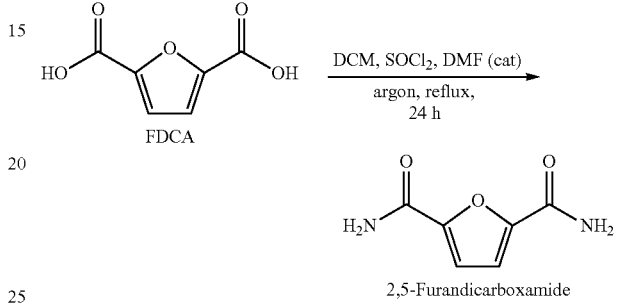

Reaction Scheme for the Synthesis of 2,5-Furandicarboxamide from FDCA

A single necked 50 mL round bottomed flask was charged with a PTFE coated magnetic spin bar 2,5-furandicarboxylic acid (1.2 g, 7.7 mmol), and dry dichloromethane. The slurry was stirred at room temperature under positive argon pressure as N,N'-dimethylformamide (0.3 mL), and thionyl chloride (10 mL freshly distilled), were added. That slurry was stirred at room temperature overnight. The mixture was heated to reflux in a 50° C. oil bath and a solution rapidly developed. The reflux was maintained for 24 hours. The excess thionyl chloride and dichloromethane was removed via rotary evaporation. The white residue in the flask was chilled in a water ice bath and the mixture was exposed to positive ammonia pressure for twenty minutes. Not much happened. To the flask was added dry tetrahydrofuran (20 mL) and the ammonia pressure (5 psig) was returned. The slurry thickened as it stirred on ice. The mixture was diluted with water (2 mL) and allowed to rest overnight. The white solid was isolated via suction filtration over a Hirsch funnel with minimal ice cold water rinsing. The filter cake was pressed dry, chopped, and spread on paper to air dry. The 2,5-furandicarboxamide was a white crystalline solid (1.1 g, 7.1 mmol, 92% yield)

$^1$H NMR (DMSO-d$_6$, 400 MHz) δ: 7.11 (s, 2H), 7.6 (br s, 2H), 8.09 (br s, 2H);

$^{13}$C NMR (DMSO-d$_6$, 100 MHz) δ: 115.1, 148.7, 159.3

E. Synthesis of 2,5-Furandicarbonitrile 7

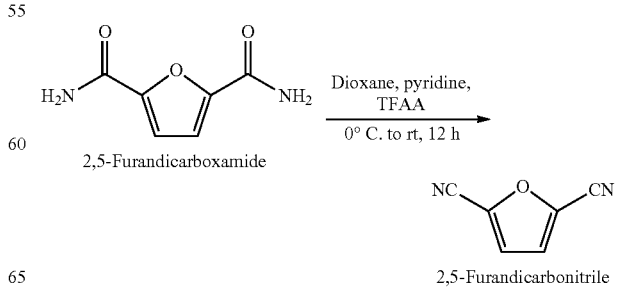

Reaction Scheme for the Synthesis of 2,5-Furandicarbonitrile 2,5-Furandicarboxamide (200 mg, 1.3 mmol, 1 equiv.) was added to flask. Dioxane (12 mL), pyridine (0.90 mL, 11.18 mmol, 8.6 equiv.) and trifluoroacetic anhydride (0.78 mL, 5.59 mmol, 4.3 equiv.) were added at 0° C. The reaction was stirred at room temperature overnight. Solvent was removed under vacuum using a rotary evaporator yielding 2,5-furandicarbonitrile as a white solid in 85 mg (55% yield).

mp=61-63° C.;

$^1$H NMR (CDCl$_3$, 400 MHz) δ: 6.12 (s, 2H);

$^{13}$C NMR (CDCl$_3$, 100 MHz) δ: 31.0, 109.5, 122.3.

F. Synthesis of 2,5-Diformylfuran from HMF 6

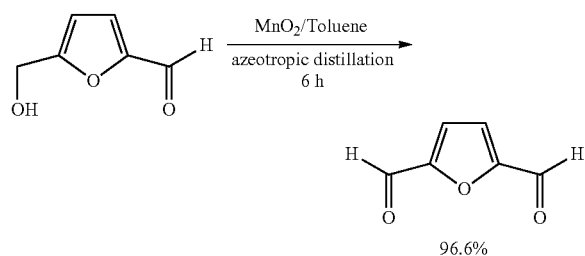

96.6%

Reaction Scheme for the Synthesis of 2,5-Diformylfuran from HMF

To a single necked (24/40) round bottomed flask was added, toluene (400 mL), 5-hydroxymethylfurfural (11.46 g, 0.0909 mol), and a PTFE coated magnetic spinning egg. The mixture was stirred vigorously pure-crystalline HMF did not fully dissolve. To that stirring mixture was added 88% active electrolytically precipitated manganese dioxide (Alfa Aesar, 11.51 g, 0.2498 mol). The black slurry was stirred vigorously, and a Dean-Stark trap was installed above the flask (topped with a Dimroth condenser plumbed with a stream of cold water). The headspace of the flask was purged with argon and the mixture was brought up to a fast boil. The flask was wrapped in aluminum foil and distillate began to collect. As the reaction proceeded, water separated to the bottom of the trap while dry toluene was allowed to return. This azeotropic distillation proceeded for six hours. The mixture was suction filtered through qualitative paper in a ceramic Buchner funnel. The residue was packed into a Soxhlet extractor and the filtrate was installed below. The Soxhlet extractor was charged from the top with enough acetone to flush the extractor five times. The mixture was brought up to boiling temperature with a heating mantle and a variable controller. The residue was continuously extracted with acetone in that manner overnight.

The heat was killed, the acetone/toluene solution was suction filtered through a bed of Celite packed into a medium porosity fritted Buchner funnel. The filtrated was a light yellow color and was concentrated by rotary evaporation under a vacuum induced by a water aspirator. The light yellow crystalline solid was scraped into a free flowing flakey solid and dried on the high vacuum line to constant mass which afforded 2,5-diformyl furan (10.89 g, 0.0878 mol, 96.6% yield).

$^1$H NMR (CDCl$_3$, 400 MHz) δ: 7.35 (s, 2H), 9.87 (s, 2H)

$^{13}$C NMR (CDCl$_3$ 100 MHz) δ: 119.3, 154.2, 179.2

G. Multistep Synthesis of 2,5-Furandipropanoic Acid 8
Synthesis of 2,5-Furylbis(Propenoic Acid) (1st Procedure)

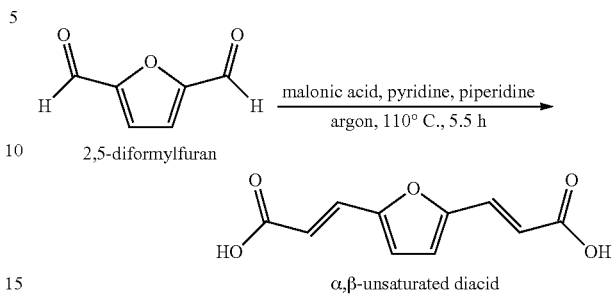

α,β-unsaturated diacid

Malonic acid (5.2039 g, 0.05 mol) was dissolved in pyridine (5.7 mL). 2,5-Diformylfuran (3.050 g, 0.025 mol) was added, followed by the slow addition of piperidine (4.9 mL, 0.05 mol). The reaction was then placed under argon and allowed to reflux. The progress of the reaction was monitored by TLC (10% MeOH/DCM) and was determined to have gone to completion after 5.5 h. 2 M HCl was prepared and slowly poured into the reaction mixture until pH 1, resulting in the precipitation of a lighter brownish-yellow solid. The solid was then filtered using suction filtration. The partially dry compound was then transferred to a roundbottom and washed with DCM. The mixture was sonicated to induce dissolution of the impurities. The washed compound was then filtered over a fritted funnel using suction filtration. The α,β-unsaturated diacid was obtained as a light brownish yellow powder in 3.3 g (63% yield).

$^1$H NMR (DMSO-d$_6$, 400 MHz) δ: 6.33 (d, J=15.6 Hz, 1H), 6.97 (s, 1H), 7.34 (d, J=16.0 Hz, 1H), 13.04 (s, 1H)

$^{13}$C NMR (DMSO-d$_6$, 100 MHz) δ: 118.2, 119.0, 130.6, 152.7, 167.8

Synthesis of 2,5-Furylbis(Propenoic Acid) (2nd Procedure)

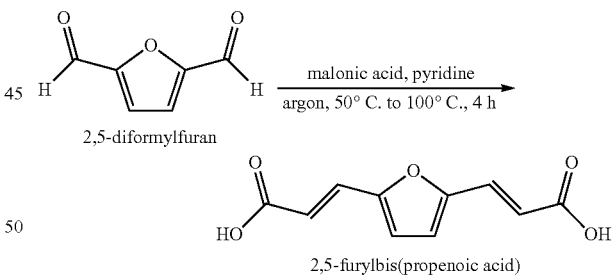

2,5-furylbis(propenoic acid)

A 25 mL single necked round bottom flask (14/20) was charged with a small spinning PTFE coated magnetic football, malonic acid (6.1 g, 59 mmol), 2,5-diformylfuran (3.3 g, 27 mmol), and pyridine (10 mL freshly distilled off of calcium hydride under argon). The slurry was thermally equilibrated with a 50° C. oil bath under a tall west condenser (plumbed with 16° C. water flow) for two hours. A solution formed rapidly upon initial heating. During that time vigorous evolution of a gas (presumed to be carbon dioxide) was observed as the color of the reaction solution transitioned to deep red (eventually black). The temperature of the oil bath was increased to 100° C. for two hours, followed by slow cooling to room temperature with stirring overnight.

Sodium hydroxide (3.5 g, 87 mmol) was dissolved in water (50 mL) and added to the reaction mixture and heated at 50° C. until a black solution formed. The black solution was diluted to circa 175 mL with distilled water and transferred to a 250 mL separatory funnel. That solution was extracted thrice with ethyl acetate (25 mL) to remove a light yellow contaminate and any residual starting material. The basic aqueous solution was decolorized with Norrit A and isolated by suction filtration through a pad of celite. The filtrate was acidified with 20 cc of concentrated hydrochloric acid in a 1 L Erlenmeyer flask. Immediately upon acidification a cream colored solid precipitated. That mixture was chilled in an ice bath and the solid was isolated by suction filtration. The filter-cake was pressed dry and the solid was spread on paper to dry for a few days to afford 2,5-furylbis (propenoic acid) (4.5 g, 21 mmol, 77% yield).

H. Synthesis of 2,5-Furylbis(Ethylpropenoate) 9

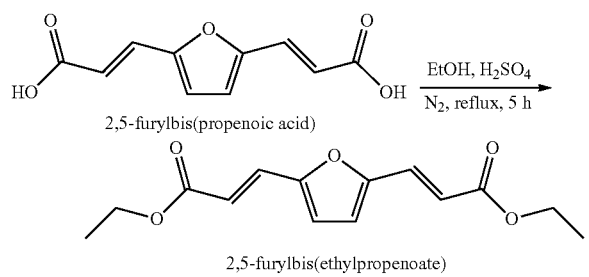

Reaction Scheme for the Synthesis of 2,5-Furylbis(Ethylpropenoate)

A 250 mL single necked round bottomed flask (joint sized 24/40) was charged with a 200 mm by 50 mm polytetrafluoroethylene coated magnetic spinning egg, 2,5-furylbis(propenoic acid) (2.08 g, 1.0 mmol), absolute ethanol (200 mL), and concentrated sulfuric acid (1.0 mL). The flask was affixed with a Dimroth condenser (plumbed with a stream of 16° C. water). The system was sealed with a red rubber serum septum and flushed with dry nitrogen. Under slight positive nitrogen pressure the system was warmed to a vigorous reflux by the action of a Thermowell and Variac. That reflux was maintained for approximately five hours and stirred overnight at room temperature (22° C.).

The mixture was concentrated to circa half of its original volume by rotary evaporation and partitioned between water/saturated sodium chloride/ethyl acetate (1:1:2×100 mL) in a 500 mL separatory funnel. The mixture was diluted with saturated sodium bicarbonate until the aqueous layer tested neutral to universal indicator paper. The ethyl acetate solution was isolated, the aqueous layer was extracted twice more with 100 mL of ethyl acetate. The organic extracts were combined, backwashed with saturated sodium chloride, isolated, dried ($Na_2SO_4$), gravity filtered and adsorbed onto 60 Å amorphous silica gel. The free flowing silica gel slurry with the crude product adsorbed was eluted with hexanes and ethyl acetate to afford a slightly yellow solution which was concentrated by rotary evaporation to yield 2,5-furylbis(ethylpropenoate) (2.17 g, 0.82 mmol, 82% yield) as a light yellow crystalline solid.

I. Synthesis of 2,5-Furylbis(Methylpropenoate) 10

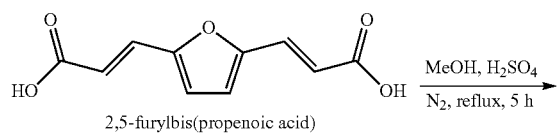

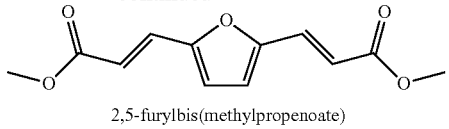

Reaction Scheme for the Synthesis of 2,5-Furylbis(Methylpropenoate)

A 250 mL single necked round bottomed flask (joint sized 24/40) was charged with a 100 mm by 25 mm polytetrafluoroethylene coated magnetic spinning egg, 2,5-furylbis(propenoic acid) (1.1 g, 0.53 mmol), HPLC grade methanol (100 mL), and concentrated sulfuric acid (0.5 mL). The flask was affixed with a Dimroth condenser (plumbed with a stream of 16° C. water). The system was sealed with a red rubber serum septum and flushed with dry nitrogen. Under slight positive nitrogen pressure the system was warmed to a vigorous reflux by the action of a Thermowell and Variac. That reflux was maintained for approximately five hours and stirred overnight at room temperature (22° C.).

The mixture was concentrated to circa half of its original volume by rotary evaporation and partitioned between water/saturated sodium chloride/ethyl acetate (1:1:2×50 mL) in a 250 mL separatory funnel. The mixture was diluted with saturated sodium bicarbonate until the aqueous layer tested neutral to universal indicator paper. The ethyl acetate solution was isolated, the aqueous layer was extracted twice more with 50 mL of ethyl acetate. The organic extracts were combined, backwashed with saturated sodium chloride, isolated, dried ($Na_2SO_4$), gravity filtered and adsorbed onto 60 Å amorphous silica gel. The free flowing silica gel slurry with the crude product adsorbed was eluted with hexanes and ethyl acetate to afford a slightly yellow solution which was concentrated by rotary evaporation to yield 2,5-furylbis(methylpropenoate) (1.1 g, 0.47 mmol, 88% yield) as a light yellow crystalline solid. The yellow color could be removed by dissolution of the target compound followed by treatment with Norrit A decolorizing carbon dust, filtration through diatomaceous earth, and subsequent concentration of the filtrate.

$^1$H NMR (CDCl$_3$, 400 MHz) δ: 3.82 (s, 6H) 6.44 (d, 2H), 6.67 (s, 2H), 7.31 (d, 2H);

$^{13}$C NMR (CDCl$_3$, 100 MHz) δ: 51.8, 116.8, 117.6, 130.3, 152.4, 167.1

J. Synthesis of 2,5-Furandipropanoic Acid 11

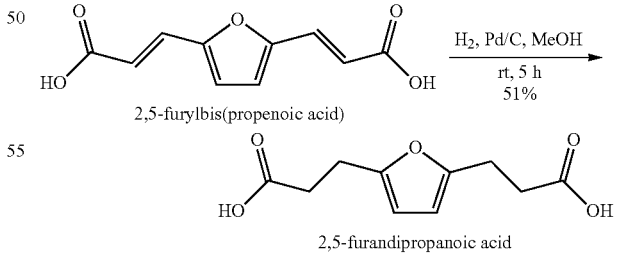

Reaction Scheme for the Synthesis of 2,5-Furandipropanoic Acid

A slurry of 2,5-furylbis(propenoic acid) (0.522 g, 2.5 mmol) and MeOH (15 mL) was prepared in a 2-neck, 50 mL rb flask. 5% Pd/C (50 mg) was added and the reaction was placed under hydrogen utilizing a vacuum pump to ensure complete removal of atmospheric air. The reaction was allowed to stir for 5 hours, and was then filtered over a bed of celite. The resulting solution was concentrated and dried using a rotary evaporator. The 2,5-furandipropanoic acid was then washed with chloroform to remove impurities. 2,5-furandipropanoic acid was obtained as a white crystalline powder in 0.2740 g (52% yield).

$^1$H NMR (400 MHz, DMSO) δ: 5.95 (s, 2H), 2.76 (t, 4H, J=12 Hz), 2.5 (t, 4H, J=12 Hz)

$^{13}$C NMR (400 MHz, DMSO) δ: 174.1, 153.4, 106.3, 32.7, 23.7.

K. Synthesis of 2,5-Furylbis(Methylpropenoate) 12

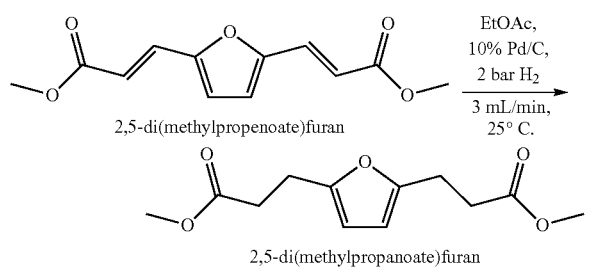

Reaction Scheme for the Synthesis of 2.5-Furylbis(Methylpropenoate)

A 0.05 molar solution of 2,5-furylbis(methylpropenoate) in ethyl acetate (72 mL, 3.6 mmol) was prepared by gently warming the solid in ethyl acetate over a water bath until dissolution was complete. Upon cooling to room temperature (22° C.) the solution was diluted to a total volume of 20 mL (to replace the ethyl acetate lost during the heating). The solution was eluted through the H cube pro system using a 10% palladium on carbon catalyst cartridge under 2 bar of hydrogen pressure at 3 mL per minute with the catalyst chamber at 25° C. The effluent was concentrated by rotary evaporation to afford 2,5-furylbis(methylpropanoate) (0.86 g, 3.6 mmol, quantitative yield) as a colorless oil.

L. Synthesis of 2,5-Furylbis(Ethylpropanoate) 13

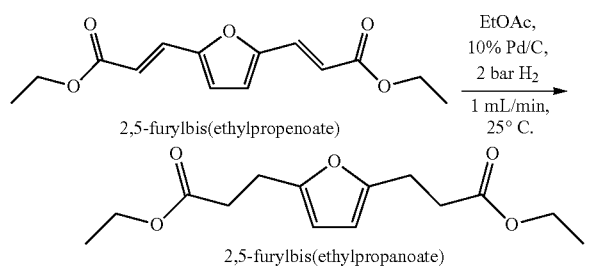

Reaction Scheme for the Synthesis of 2,5-Furylbis(Ethylpropanoate)

A 0.05 molar solution of 2,5-furylbis(ethylpropenoate) in ethyl acetate (20 mL, 1.0 mmol) was prepared by gently warming the solid in ethyl acetate over a water bath until dissolution was complete. Upon cooling to room temperature (22° C.) the light yellow solution was diluted to a total volume of 20 mL (to replace the ethyl acetate lost during the heating). The solution was eluted through the H cube pro system using a 10% palladium on carbon catalyst cartridge under 2 bar of hydrogen pressure at 1 mL per minute with the catalyst chamber at 25° C. The effluent (much lighter in color after passage through the flow system) was concentrated by rotary evaporation to afford 2,5-furylbis(ethylpropanoate) (0.23 g, 0.96 mmol, 96% yield) as a light yellow oil.

M. Synthesis of 2,5-Bis(Hydroxymethyl)Furan 3

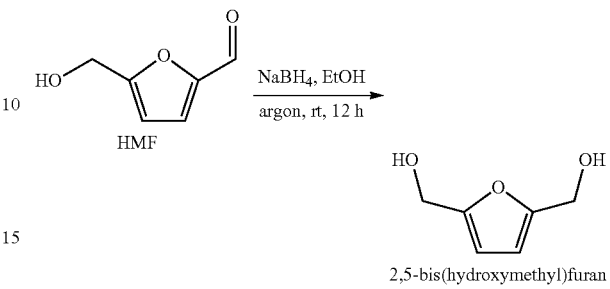

Reaction Scheme for the Synthesis of 2,5-Bis(Hydroxymethyl)Furan from HMF

Hydroxymethylfurfural (10.0 g, 0.079 mol) was dissolved in absolute EtOH (100 mL) and cooled to 0° C. Sodium borohydride, NaBH$_4$ (2.0 mg, 0.053 mol) was slowly added. The reaction flask was then sealed and allowed to stir for 12 h. The EtOH was evaporated under reduced pressure using a rotary evaporator. Pure compound was obtained by column chromatography using Dichloromethane-Methanol (95:5) as an eluent and silica gel (300-400 Mesh) as a stationary phase. The 2,5-bis(hydroxymethyl)furan was obtained as a white crystalline powder in 7.5 g (74% yield). mp=75-77° C.;

1H NMR (DMSO-d$_6$, 400 MHz) δ: 4.28 (s, 2H), 6.11 (s, 1H);

$^{13}$C NMR (DMSO-d$_6$, 100 MHz) δ: 56.3, 108.0, 155.2

N. Synthesis of 5-Hydroxymethyl-2-Furanacrylic Acid from HMF

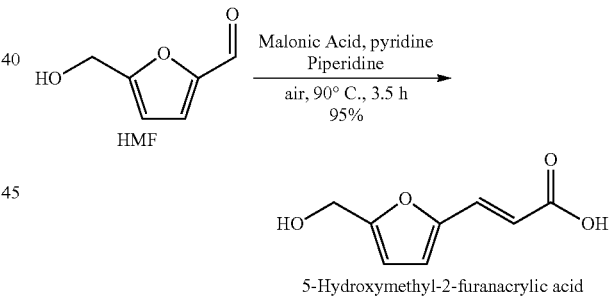

Reaction Scheme for Synthesis of 5-Hydroxymethyl-2-Furanacrylic Acid from HMF

The 5-hydroxymethyl-2-furanacrylic acid was prepared from HMF using the Doebner Modification of the Knoevenagel Condensation (Skowroński et al., *Org. Prep. Proced. Int.* 1993, 25, 353). The HMF (1.2634 g, 10 mmol), malonic acid (2.081 g, 20 mmol), and piperidine (69.1 µL, 0.7 mmol) were dissolved in pyridine (4.0 mL, 49.7 mmol). A guard tube was attached and the reaction was allowed to reflux at 90° C. The reaction progress was checked using thin layer chromatography (TLC). After 5 hours the reaction was determined to have gone to completion. The reaction was quenched using 1 M HCl until a pH≤1 was achieved. The desired compound was then extracted using ether (25 mL, 2× and 30 mL, 4×). The solvent was then evaporated under reduced pressure to yield a yellowish orange crystalline powder in 1.612 g (95%).

$^{1}$H NMR (DMSO-d$_6$, 400 MHz) δ: 2.44 (s, 2H), 6.04 (d, J=14.6 Hz, 1H), 6.37 (d, J=14.6 Hz, 1H), 6.79 (d, J=7.2 Hz, 1H), 7.29 (d, J=7.2 Hz, 1H), 13.24 (s, 1H);

$^{13}$C NMR (DMSO-d$_6$, 100 MHz) δ: 56.4, 110.3, 115.9, 117.1, 131.5, 150.2, 159.0, 168.1.

O. Synthesis of 5-Formyl-2-Furanacrylic Acid

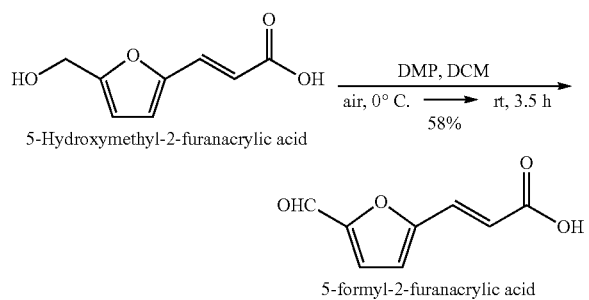

Reaction Scheme for Synthesis of 5-Formyl-2-Furanacrylic Acid

The prepared 5-hydroxymethyl-2-furanacrylic acid was oxidized using the Dess Martin oxidation reaction to form 5-formyl-2-furanacrylic acid (Steurer et al. *J. Eur. J. Org. Chem.* 1999, 1551). Dess Martin Periodinane, DMP (0.318 g, 0.75 mmol) was dissolved in the solvent dichloromethane, DCM (2 mL). The solution was then allowed to cool to 0° C. In a separate flask, the 5-hydroxymethyl-2-furanacrylic acid was partially dissolved in 5 mL of DCM and transferred dropwise into flask containing DMP. An additional 3 mL of DCM was added to transfer remaining 5-hydroxymethyl-2-furanacrylic acid which again was added dropwise into flask containing the DMP. The reaction was then allowed to warm to room temperature naturally and stir for 3.5 h in open atmosphere. The reaction was filtered over a glass fritted funnel. The solid and organic layers were checked using TLC with DNP staining which indicated the desired aldehyde compound was located in the solvent layer. The DCM was then evaporated under reduced pressure using a rotary evaporator to yield the product in 0.0487 g (58%)

P. Synthesis of 5-Carboxy-2-Furanacrylic Acid

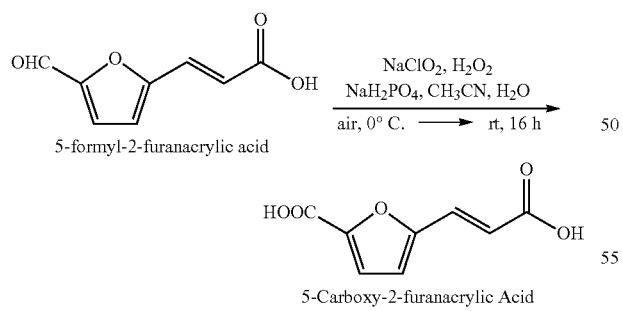

Reaction Scheme for Synthesis of 5-Carboxy-2-Furanacrylic Acid

5-Formyl-2-furanacrylic acid (0.048 g, 0.29 mmol) was dissolved in acetonitrile, CH$_3$CN (1 mL). To this, NaH$_2$PO$_4$ (13.1 mg, 0.11 mmol) dissolved in water (0.5 mL) was added. The reaction mixture was then allowed to cool to 0° C. 30% H$_2$O$_2$ (0.2 mL) was then added. NaClO$_2$ (0.39 g, 0.43 mmol) in 1 mL H$_2$O was then slowly added dropwise over 15 minutes. The reaction was then allowed to cool to room temperature naturally and allowed to stir for 16 h. Excess water was then added and the desired compound was extracted. $^{1}$H NMR was obtained. $^{1}$H NMR (400 MHz, DMSO) δ: 7.38 (d, 1H, J=16 Hz), 7.24 (d, 1H, J=4 Hz), 7.03 Hz (d, 1H, J=4 Hz), 6.31 Hz (d, 1H, J=16 Hz)

Q. Extension to Other Furan-Derived Monomers

A wide variety of monomers can be readily synthesized from the base monomers described in sections A through P, above, using reactions described herein and, optionally in some instances, other chemical reactions known to the art for interconversion and extension of organic monomers containing carboxyl, aldehyde, alcohol, amine, allyl, and other functional groups. Importantly, the base monomers described herein can be used to generate other disubstituted monomers, such as dicarboxylic acids, dialdehydes, diols, diamines, and the like. Exemplary monomers that can be synthesized from base monomers derived from biomass and/or described herein using synthetic methods described herein and, optionally, other interconverstion and extension methods known to the art are shown below. These disubstituted monomers can be symmetrical or asymmetrical. The generation of asymmetrical disubstituted monomers, as well as the monomers so generated, represent aspects of the invention that are expected to be especially useful in the industrial polymer industry, opening up many possibilities for novel bio-based polymers and copolymers.

Symmetrical and Unsymmetrical Furan Dicarboxylic Acids

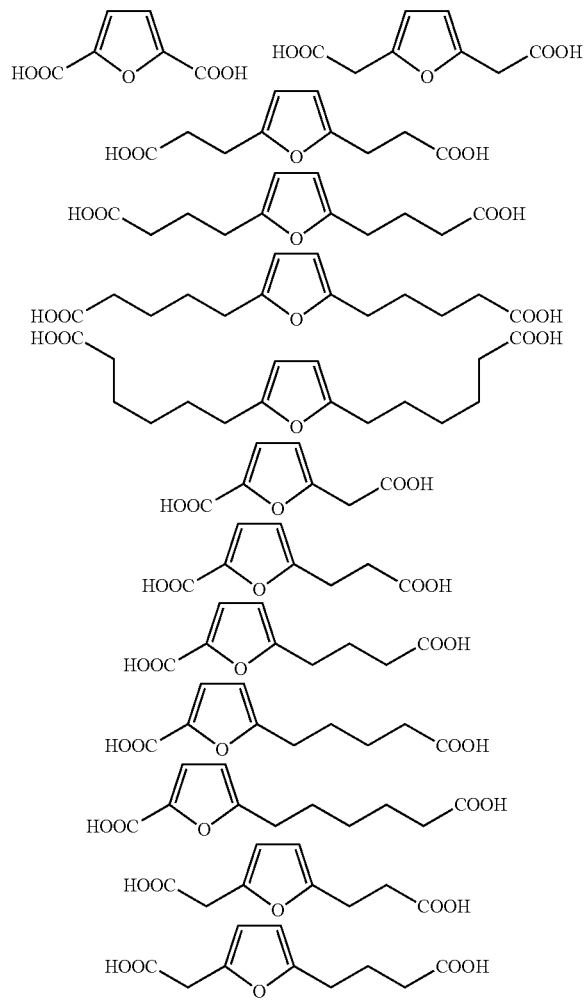

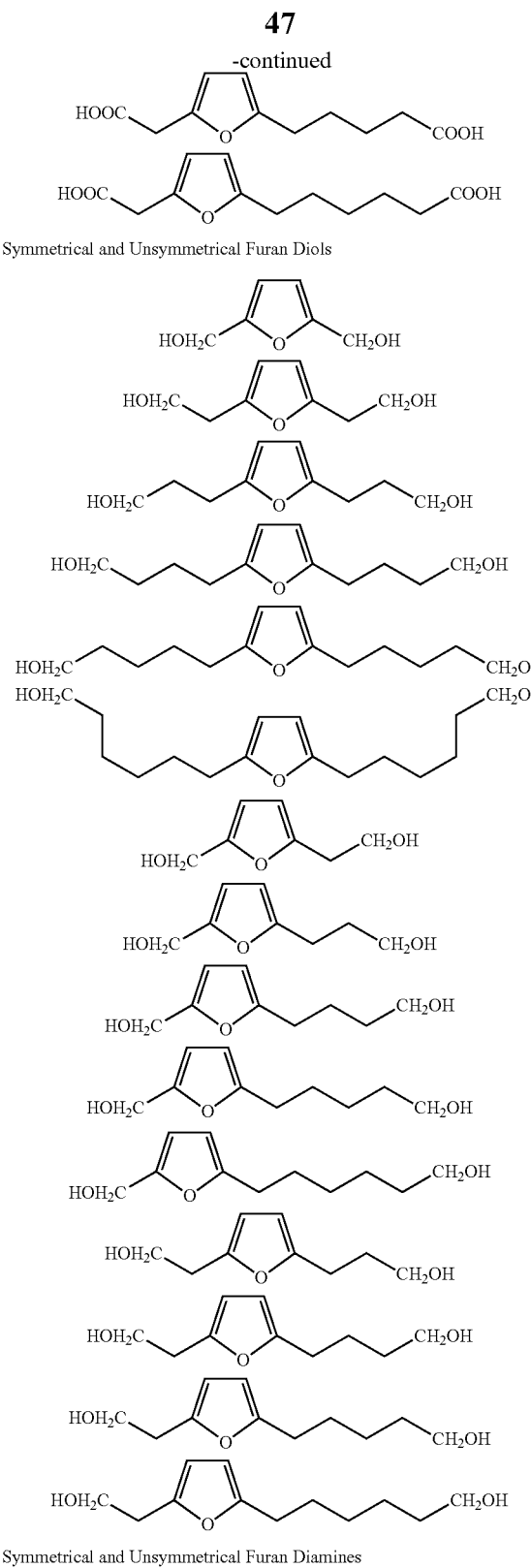

Symmetrical and Unsymmetrical Furan Diols

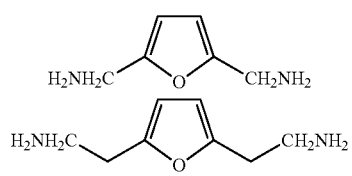

Symmetrical and Unsymmetrical Furan Diamines

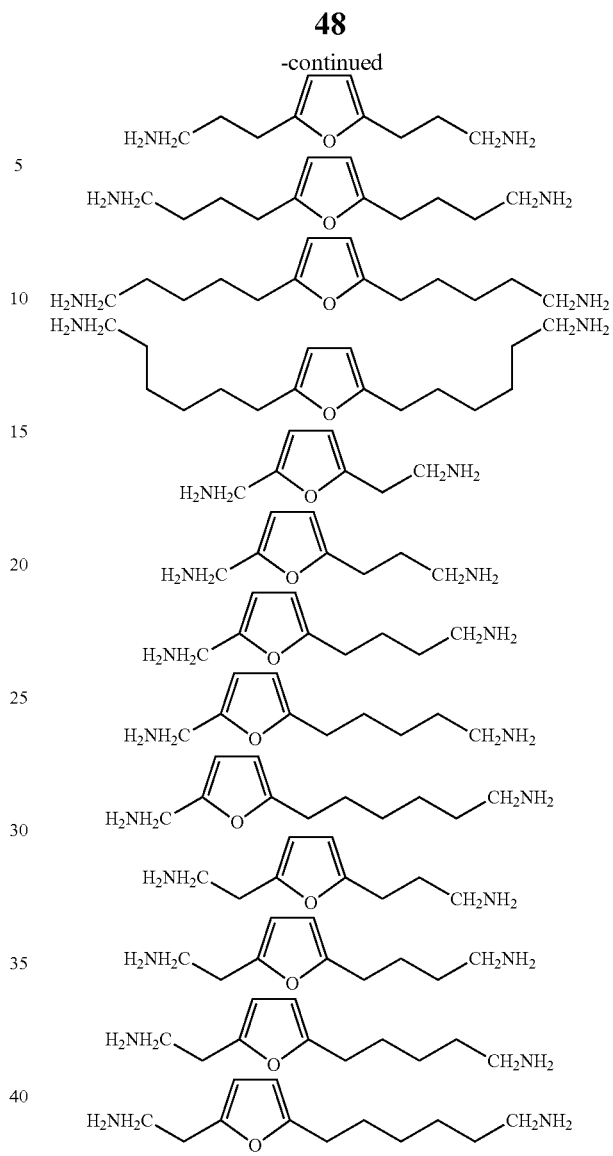

Example II

Synthesis of Naphthalene Diacids from Cellulosic Biomass Using Diels-Alder Methodology Furan monomers described in Example I have been utilized in the synthesis of naphthalene based terephthalic acid analogs using a two-step protocol. The key step is the Diels-Alder reaction of furan with benzyne. This is followed by a deoxygenation/aromatization step to provide naphthalene derivatives. Using this strategy we have synthesized several naphthalene derivatives.

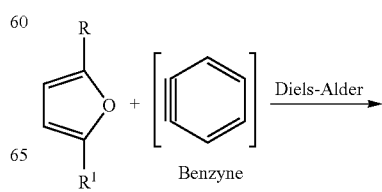

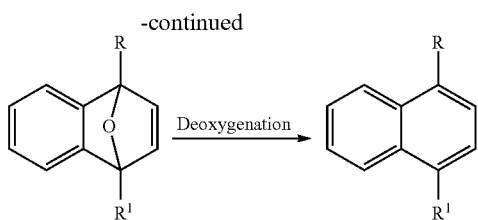

General Procedure for the Diels Alder Reaction Between Benzyne Precursor and Furan Derivatives:

To a vigorously stirred solution of furan derivative (2.0 mmol) and CsF (4.4 mmol) in CH₃CN (24 mL) was added a solution of 2-(trimethylsilyl)phenyl trifluoromethanesulfonate (2.6 mmol) in CH₃CN (24 mL) dropwise by syringe pump over 16 hours at given temperature (see the table below). After completion of the reaction (judged by thin layer chromatography), the reaction mixture was diluted with diethyl ether (100 mL) and water (50 mL). The biphasic mixture was extracted with diethyl ether (30 mL×3) and the combined organic phases were dried over anhydrous sodium sulfate. Solvent was evaporated under vacuum and the residue was purified by column chromatography using (10:1) hexane/ethyl acetate as eluent.

Substrate Scope for the Diels-Alder Reaction Between Benzyne Precursor and Furan Derivatives

| Entry | R¹ | R² | temp (° C.) | yield (%)[a] |
|---|---|---|---|---|
| 1 | Me | Me | rt | 97 |
| 2 | CH₂OBz | CH₂OBz | rt | 43 |
| 3 | CH₂OBz | CH₂OBz | 70 | 91 |
| 4 | CO₂Me | CO₂Me | rt | 38 |
| 5 | CO₂Me | CO₂Me | 70 | 87 |
| 6 | CN | CN | 70 | 64 |
| 7 | CH₂OH | CH₂OH | rt | NR |
| 8 | CH₂CH₂COOMe | CH₂CH₂COOMe | rt | >99% |
| 9 | CH₂OH | CHO | rt or 70 | NR |
| 10 | CHO | CHO | rt or 70 | NR |
| 11 | CH₂OBz | CHO | rt or 70 | NR |
| 12 | COOH | COOH | 70 | NR |

[a]Isolated yield.

General Procedure for the Deoxygenation of Diels-Alder Adduct:

Method A:

A suspension of LiAlH₄ (5.2 mmol) in THF (8 mL) was added dropwise to a solution of TiCl₄ (13 mmol) in THF (5 mL) at 0° C. and was followed by triethylamine (1.8 mmol) in THF (1 mL). The mixture was refluxed for 30 min, and then it was allowed to cool to room temperature. A solution of Diels-Alder adduct (2 mmol) in THF (3 mL) was added to the above mixture and allowed to stir for 24 h. The reaction mixture was poured into 20% aqueous K₂CO₃ (80 mL) and H₂O (20 mL). The resulting mixture was filtered, and washed thoroughly with CH₂Cl₂. The filtrate was extracted with CH₂Cl₂ (10 mL×3). The combined CH₂Cl₂ layers were dried over anhydrous sodium sulfate. Solvent was evaporated under vacuum and the residue was purified by column chromatography using (10:1) hexane/ethyl acetate as eluent.

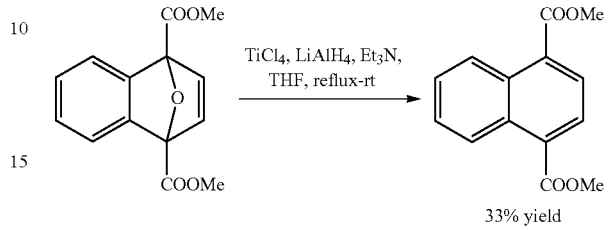

33% yield

Method B:

To a solution of Diels-Alder adduct (0.5 mmol) and NaI (2.5 mmol) in CH₃CN (40 mL), TMSCl (2.5 mmol) was added dropwise at 0° C. The reaction mixture was then stirred at room temperature for 24 h. Saturated NaHSO₃ solution (20 mL) was added and the mixture was extracted with CHCl₃ (20 mL×2). The combined CHCl₃ layers were dried over anhydrous sodium sulfate. Solvent was evaporated under vacuum and the residue was purified by column chromatography using (10:1) hexane/ethyl acetate as eluent.

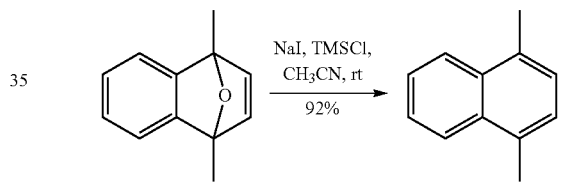

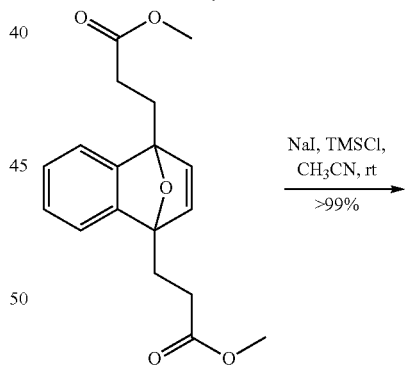

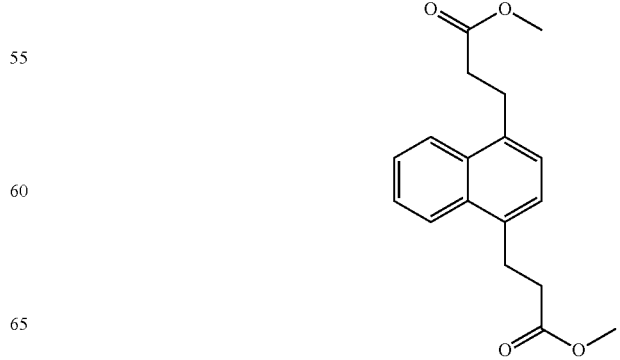

51

-continued

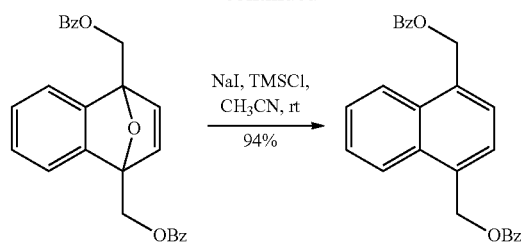

Green Method A

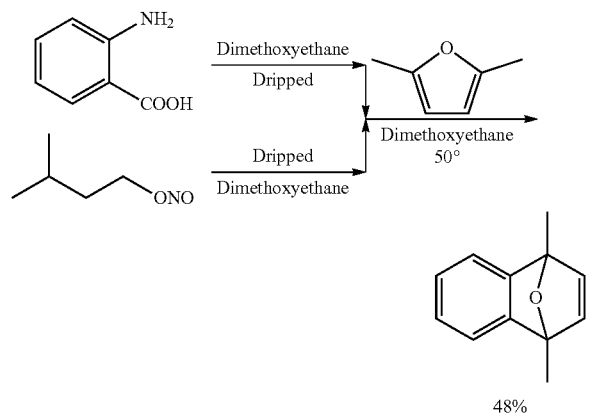

To a vacuum-flame dried single necked round bottomed flask (24/40) was added a PTFE coated magnetic spin bar, dry dimethoxyethane (20 mL freshly distilled off of sodium-benzophenone ketyl), dimethyl furan (10 mL) and the light yellow solution was warmed in an oil bath (50° C.) under an argon balloon. A solution of isopentyl nitrite in dry dimethoxyethane (10 mL in 10 mL) was drawn up into a syringe. A slurry of anthranilic acid (recrystallized from water and vacuum dried for three days) and dimethoxyethane (7.0 g, 50 mmol in 15 mL) was dispersed and drawn up into a syringe. The nitrite solution and the anthranilic acid slurry were dripped into the warm and stirring dimethyl furan solution (simultaneously) over the course of four hours via syringe pumps. During the addition, the reaction mixture turned quite red and bubbled. Upon completion of the addition, the reaction mixture was stirred at 50° C. for three hours, and then overnight at room temperature.

The reaction mixture was concentrated via rotary evaporation to thick red oil. The red residue was partitioned between diethyl ether and water. The ethereal solution was washed with weak sodium hydroxide solution, saturated sodium bicarbonate, and saturated sodium chloride. The orange solution was dried (Na$_2$SO$_4$), and adsorbed onto silica gel and combiflashed with ethyl acetate and hexanes. The peak with greatest magnitude on the chromatogram was the product. The fractions containing the product were combined and concentrated via rotary evaporation to afford 1,4-dimethyl-1,4-epoxy-1,4-dihydronaphthalene (4.1 g, 24 mmol, 48% based on anthranilic acid) as a light yellow oil.

52

Green Method B

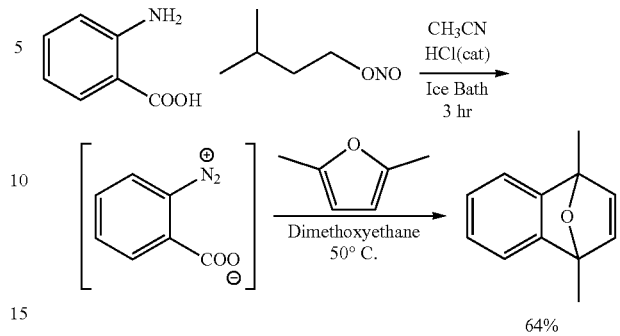

A 100 mL single necked round bottomed flask (14/20) was charged with a PTFE coated spin bar, anthranilic acid (1.4 g, 10 mmol), and HPLC grade acetonitrile (12 mL). The mixture was submerged into an ice bath above a stirplate. A single drop of concentrated hydrochloric acid from tip of a long Pasteur pipette was added to the mixture which could be described as an off white slurry. Isopentyl nitrite (1.3 g, 11 mmol) was added dropwise. Within minutes of the complete addition of isopentyl nitrite, the mixture had formed a thick, brick red slurry. That mix was stirred on ice for three hours. A solution of dimethyl furan in dimethoxyethane was prepared (1.3 g, 14 mmol, in 15 mL) and warmed in an oil bath (50° C.) in a 250 mL beaker. The brick red slurry was broken up and dispersed with dry dimethoxyethane (20 mL) and the mixture became salmon colored. The salmon colored diazonium-2-carboxylate slurry was (ice cold) was poured into the dimethylfuran solution. The mixture was stirred as the oil bath equilibrated back to 50° C. Gas evolution was noted initially but fell off by 30 minutes of reaction time. Stirring at 50° C. continued another 40 minutes and at room temperature overnight. The reaction mixture was worked up as in Green Method A to afford 1,4-dimethyl-1,4-epoxy-1,4-dihydronaphthalene (1.1 g, 6.4 mmol, 64% based on anthranilic acid) as a light yellow oil.

Green Method C

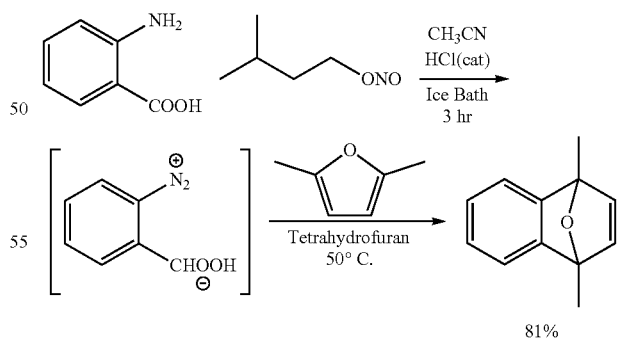

Three 18×150 mm disposable test tubes were each charged with anthranilic acid (0.9 g, 6.6 mmol), small PTFE coated spin bars, acetonitrile (10 mL), and the tubes were chilled in an ice bath. To each tube was added, isopentyl nitrite (1.0 mL, 0.87 g, 7.4 mmol); the solution carrying the solid became orange. To each was added 0.1 mL of hydrochloric acid in acetonitrile (from a stock solution of 1.0 mL of concentrated hydrochloric acid in 20 mL of acetonitrile). The reaction mixtures rapidly turned brick red. The slurries were stirred for three hours on ice. A solution of dimethyl furan in dry tetrahydrofuran (1.1 mL, 0.98 g, 1.0 mmol in 30 mL) was prepared in a 250 mL single necked round bottomed flask (24/40) and was stirred in an oil bath (50° C.). The mature slurries were poured into the dimethylfuran solutions one at a time with 30 minutes of latent time in between and a final 30 minutes of stirring at 50° C. following the last addition. The reaction mixture was worked up as in Green Methods A and B (with the notable addition of a period of treatment with decolorizing charcoal prior to combiflash) to afford 1,4-dimethyl-1,4-epoxy-1,4-dihydronaphthalene (1.4 g, 8.3 mmol, 81% based on dimethyl furan) as a light clear oil.

Dimethyl Naphthalene-1,4-Dicarboxylate

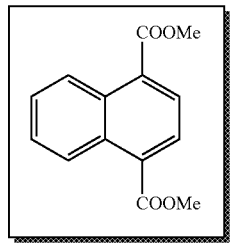

Yield: 33%

White solid $^1$H NMR (500 MHz, CDCl$_3$) δ: 4.04 (s, 6H), 7.66 (m, 2H), 8.10 (s, 2H), 8.83 (m, 2H).

HRMS: Calcd. for C$_{14}$H$_{12}$O$_4$Na+ 267.0628; Found 267.0628.

Dimethyl 3,3'-(naphthalene-1,4-diyl)dipropanoate

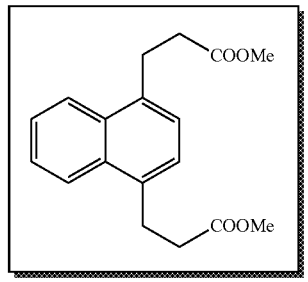

Yield: >99%

Yellow solid $^1$H NMR (400 MHz, CDCl$_3$) δ: 2.73 (m, 4H), 3.36 (m, 4H), 3.67 (s, 6H), 7.24 (s, 2H), 7.52 (dd, J=6.4, 3.2 Hz, 2H), 8.03 (dd, J=6.8, 3.2 Hz, 2H).

$^{13}$C NMR (100 MHz, CDCl$_3$) δ: 28.3, 35.1, 51.8, 124.4, 125.8, 126.0, 132.2, 135.6, 173.6. HRMS: Calcd. for C$_{18}$H$_{20}$O$_4$Na+ 323.1254; Found 323.1249.

Symmetrical and Unsymmetrical Naphthalene Diacids

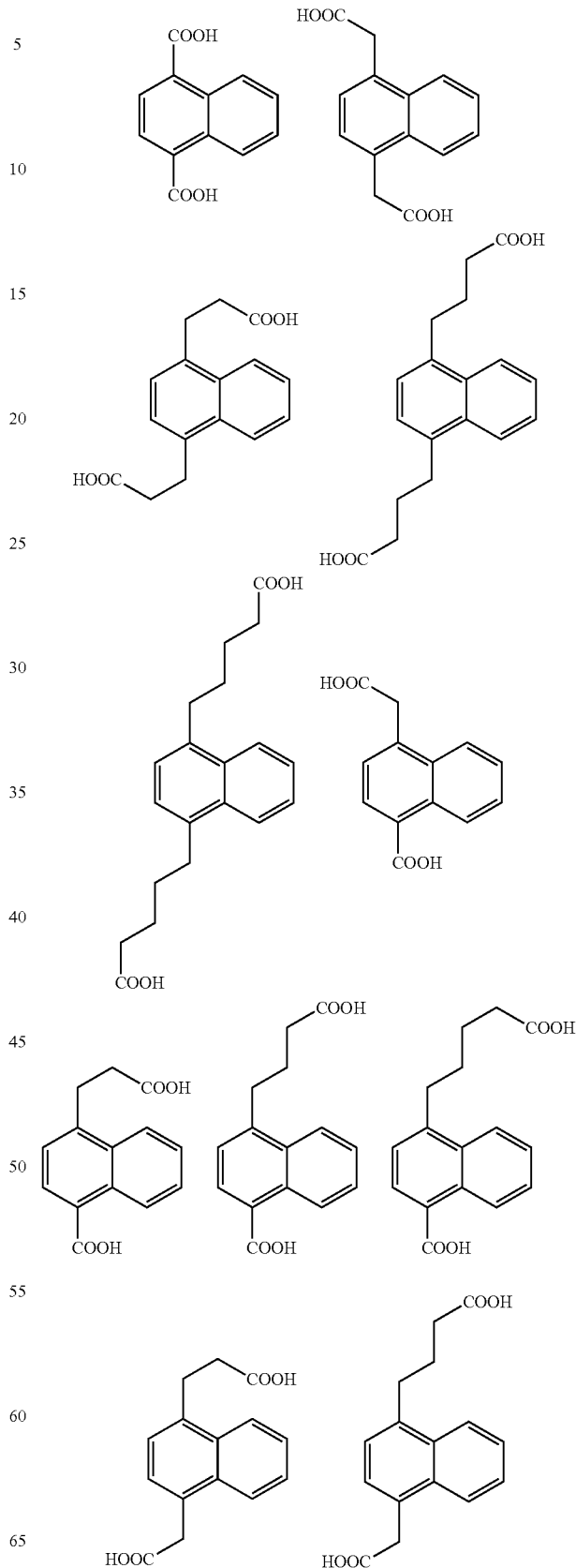

-continued
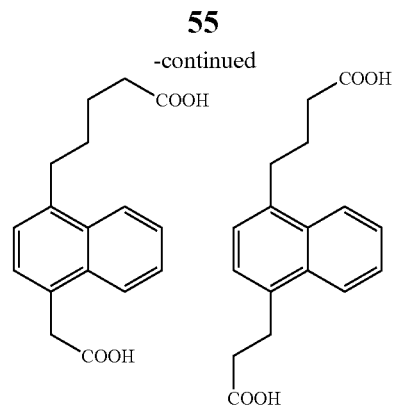
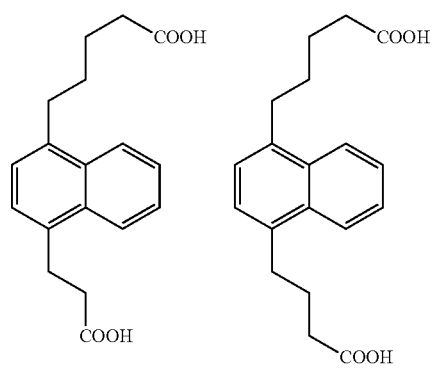
Symmetrical and Unsymmetrical Naphthalene Diamines
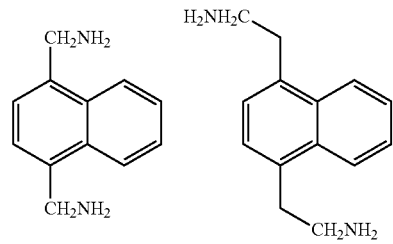
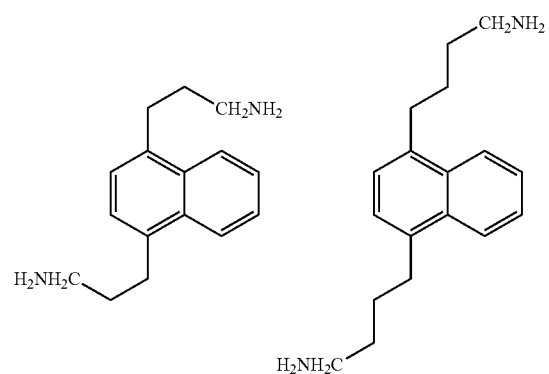
-continued
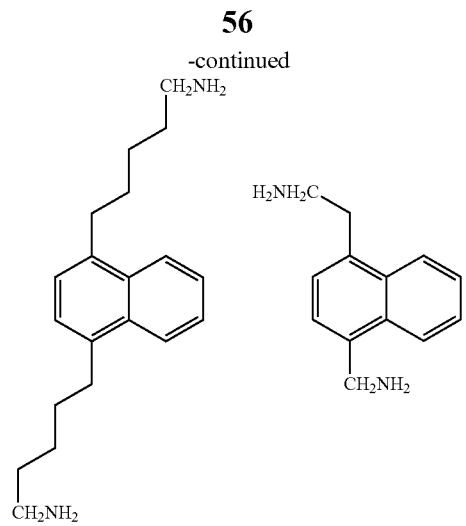
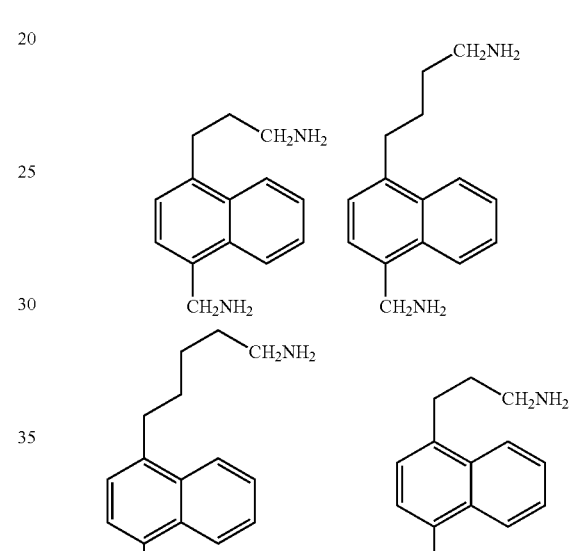
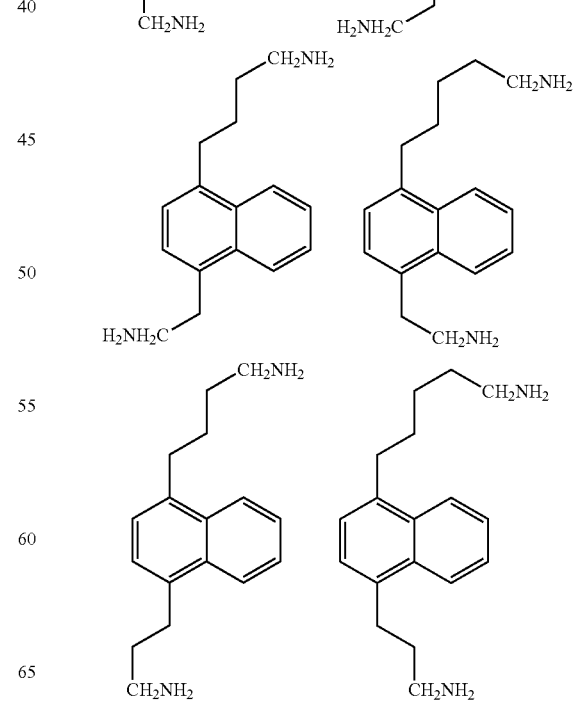

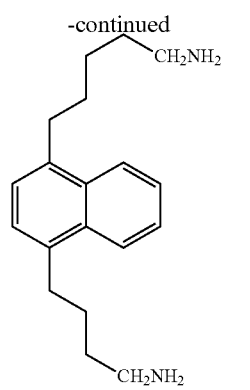
Symmetrical and Unsymmetrical Naphthalene Diols
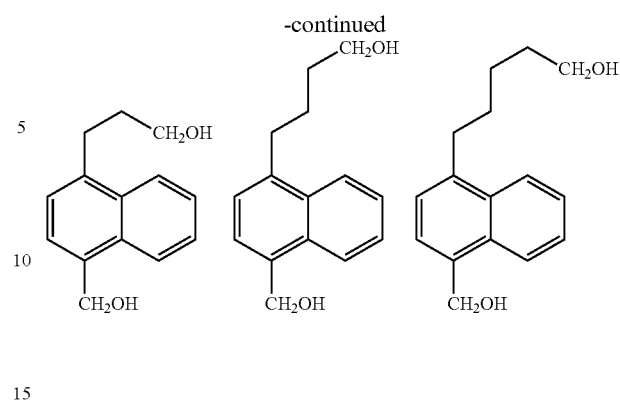
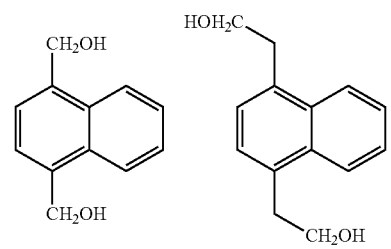
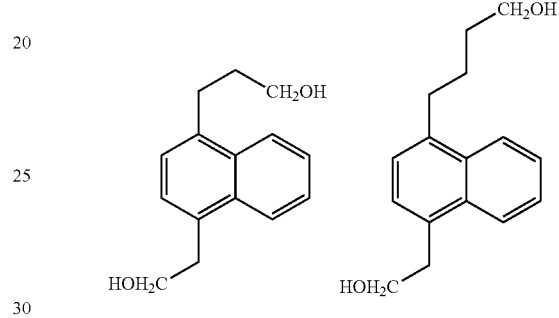
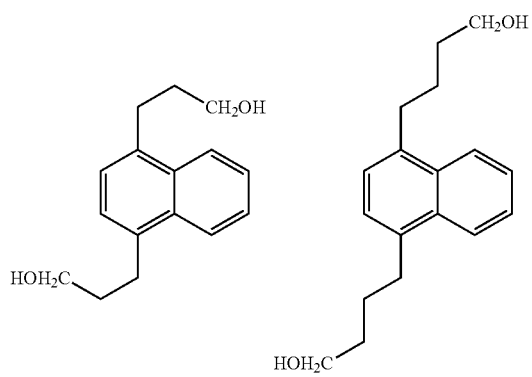
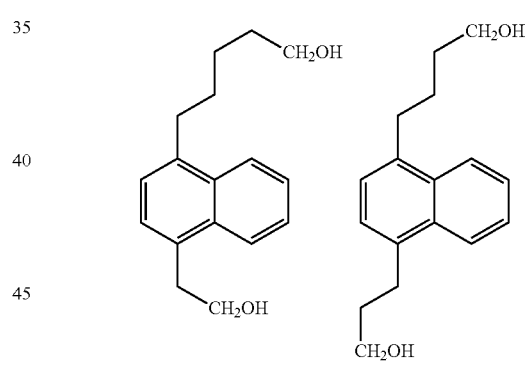
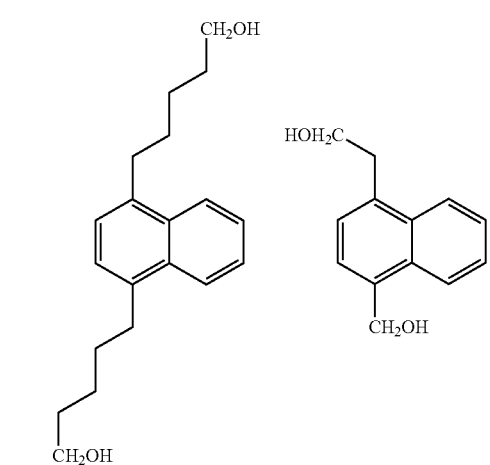
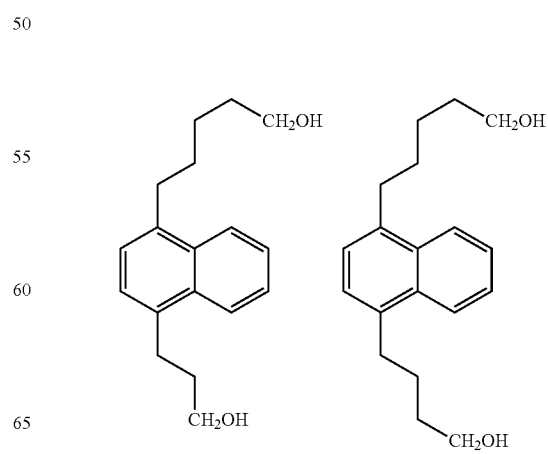

-continued
Symmetrical Naphthalene Tetraacids from Stobbe Condensation

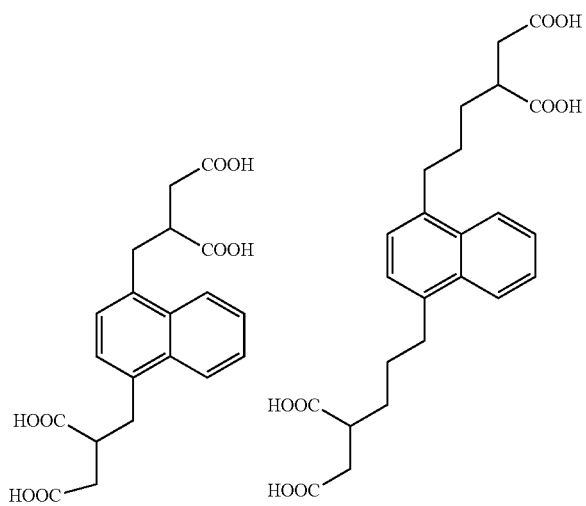

Example III

Synthesis of Furan Monomers from a Dimer of 5-Hydroxymethylfurfural (HMF)

The scheme below outlines methods for the conversion of 5-hydroxymethylfurfural (HMF) to its dimer, cirsiumaldehyde, via a condensation. The dimer is then used to prepare a variety of monomers. Procedures for the synthesis of various monomers are detailed.

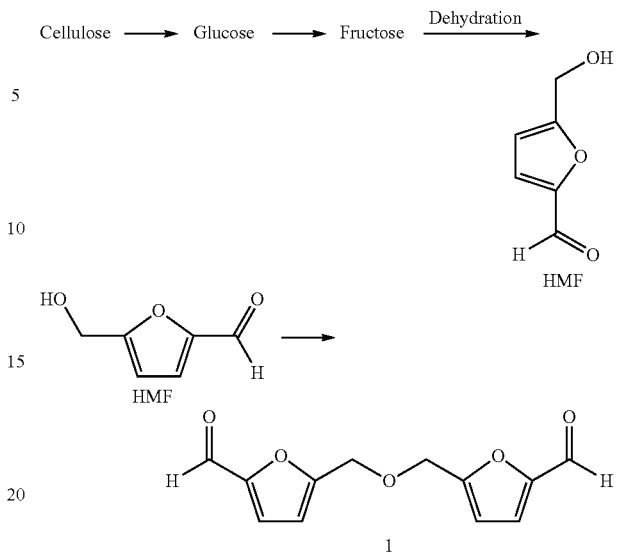

Synthesis of Cirsiumaldehyde 1

To a single necked round bottomed flask (25 mL) was added a PTFE coated magnetic spin bar, toluene (12 mL), hydroxymethylfurfural (1.0 g, 7.9 mmol), and p-toluene sulfonic acid monohydrate (0.09 g, 0.5 mmol). The mixture was fitted with a Dean-Stark trap under a Dimroth condenser (plumbed with 18° C. water flow) and heated by heating mantle and Variac until water was collected in the distillate. Reflux was continued for one hour following the first collection. The reaction mixture consisted of a black coating upon the walls of the flask and a dark toluene solution which was decanted to a fresh flask. The residue was broken up with a metal spatula under acetone and added to the same flask. The crude reaction mixture was adsorbed onto silica gel and combiflashed using hexanes and ethyl acetate. The major peak on the chromatogram was the product which was cleanly resolved from impurities. The fractions containing the product were combined and concentrated by rotary evaporation to afford cirsiumaldehyde (0.71 g, 3.0 mmol, 75% yield) as an amber crystalline solid.

Synthesis of Diacid 2

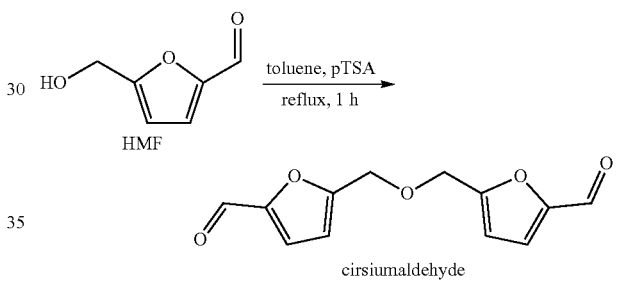

61

-continued

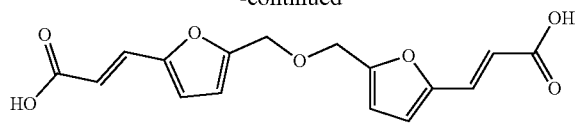

A 25 mL single necked round bottom flask (14/20) was charged with a small spinning PTFE coated magnetic football, malonic acid (6.1 g, 59 mmol), cirsiumaldehyde (5.7 g, 24 mmol), and pyridine (10 mL freshly distilled off of calcium hydride under argon). The slurry was thermally equilibrated with a 50° C. oil bath under a tall west condenser (plumbed with 16° C. water flow) for two hours. A solution formed rapidly upon initial heating. During that time vigorous evolution of a gas (presumed to be carbon dioxide) was observed as the color of the reaction solution transitioned to deep red (eventually black). The temperature of the oil bath was increased to 100° C. for two hours, followed by slow cooling to room temperature with stirring overnight.

Sodium hydroxide (3.5 g, 87 mmol) was dissolved in water (50 mL) and added to the reaction mixture and heated at 50° C. until a black solution formed. The black solution was diluted to circa 250 mL with distilled water and transferred to a 500 mL separatory funnel. That solution was extracted thrice with ethyl acetate (40 mL) to remove any residual starting material. The basic aqueous solution was decolorized with Norrit A and isolated by suction filtration through a pad of celite. The filtrate was acidified with 20 mL of concentrated hydrochloric acid in a 1 L Erlenmeyer flask. Immediately upon acidification a gray colored solid precipitated. That mixture was chilled in an ice bath and the solid was isolated by suction filtration. The filter-cake was pressed dry and the solid was spread on paper to dry for a few days to afford the title compound (6.9 g, 22 mmol, 92% yield).

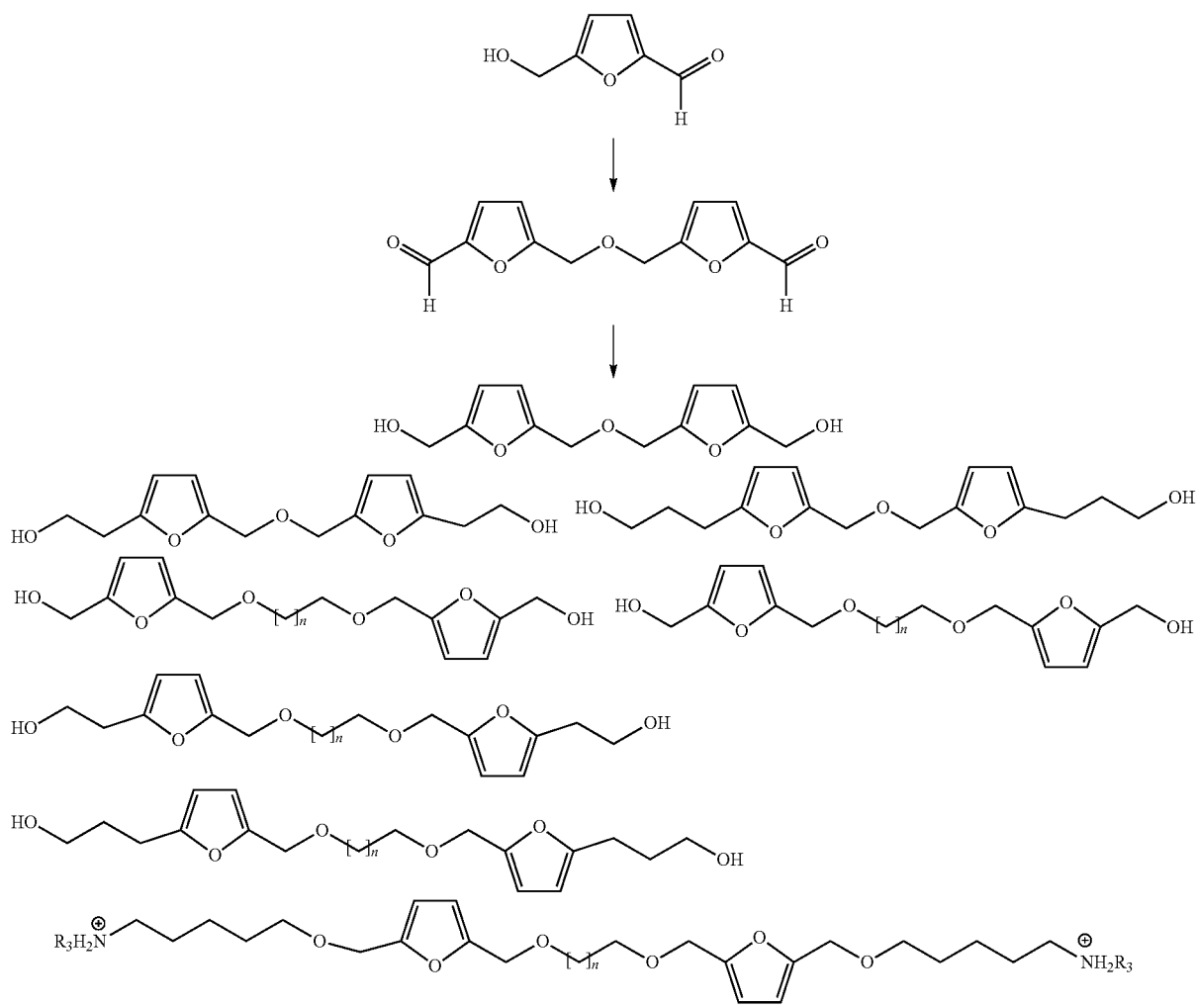

We can aslo make polyesters, polyamides, urethanes, etc.

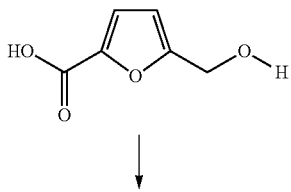

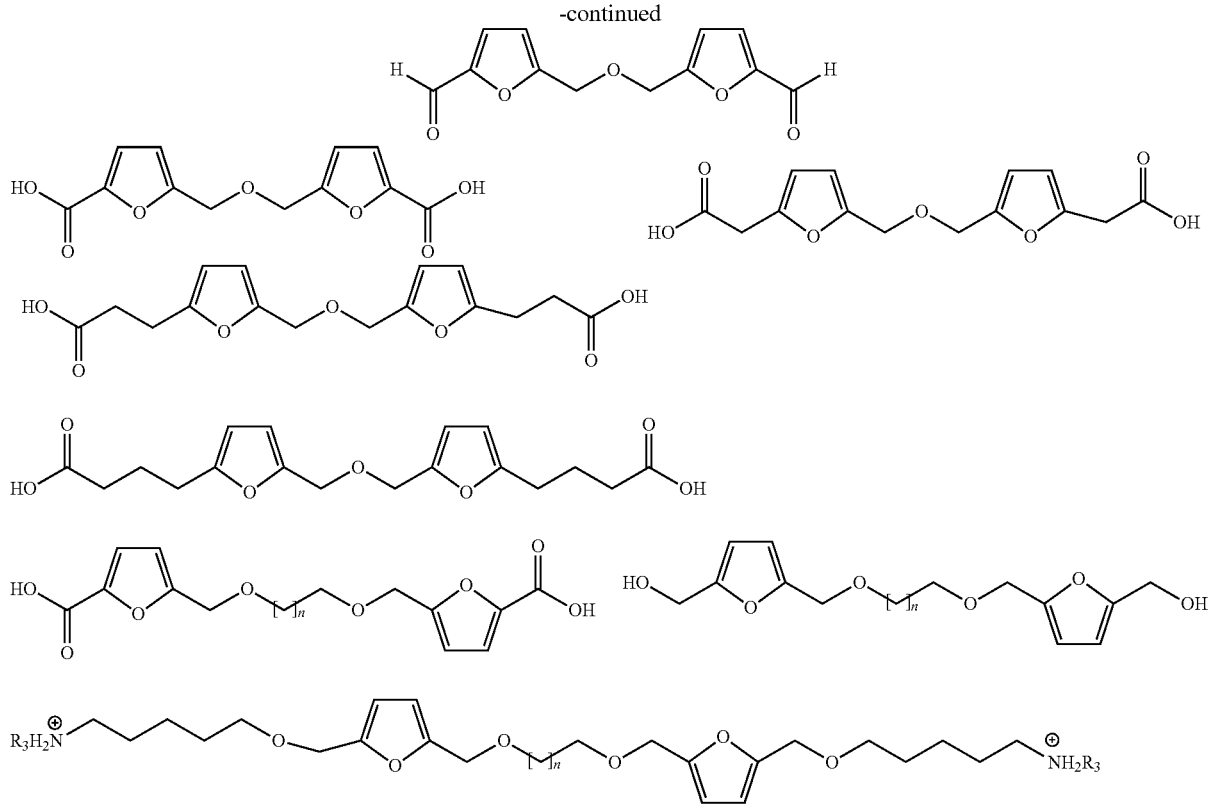

We can aslo make polyesters, polyamides, urethanes, etc.

Example IV

Synthesis of Aromatic Diacids from Lignin Monomers

Synthesis of Model Aromatic Diacids from Lignins

The major components of polymeric lignin are the following phenols. They are biosynthesized in nature starting from the amino acid phenyl alanine. The three compounds vary in their structure and in the number of methoxy groups. Lignin depolymerization leads to these alcohols as well as other phenolics

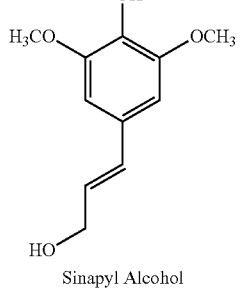

Sinapyl Alcohol

There are five important compounds that are derivatives of the primary components of lignin. Their structures are shown below. These compounds can also be found in other renewable resources.

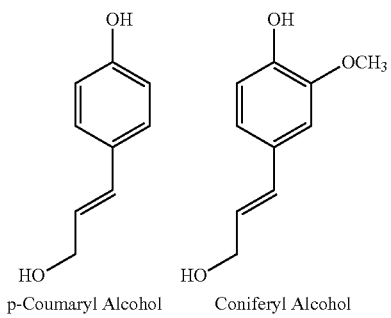

p-Coumaryl Alcohol    Coniferyl Alcohol

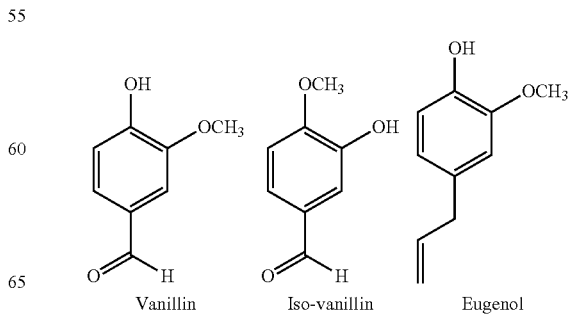

Vanillin    Iso-vanillin    Eugenol

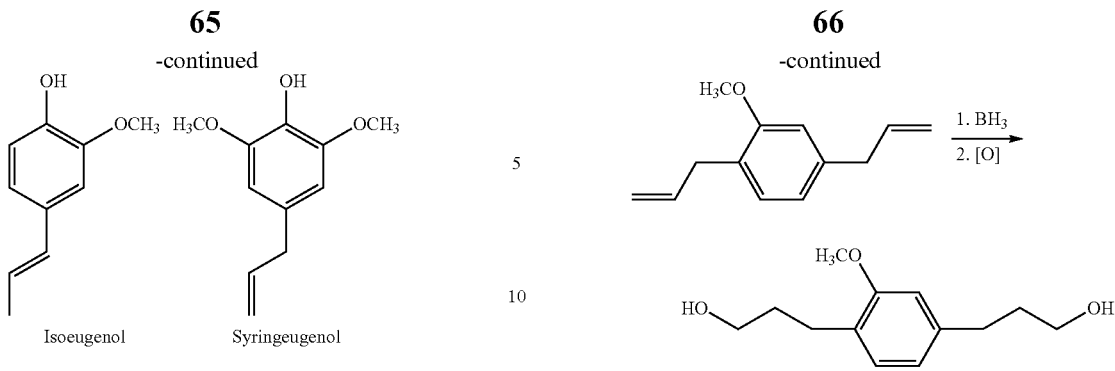

Isoeugenol     Syringeugenol

These feedstock materials can be converted into monomers for polymer preparation. A general outline of the methodology is shown below using eugenol as the starting material. The first step is the conversion of the phenolic hydroxyl to a leaving group using a cheap phosphorus derivative. This is followed by the introduction of a three-carbon fragment using a nickel catalyst. Further modification provides a variety of monomers: acids, alcohols, amines, and poly acids. The coupling step can be varied easily and carbon fragments of differing chain lengths can be incorporated, thus providing an approach to terephthalic acid analogs.

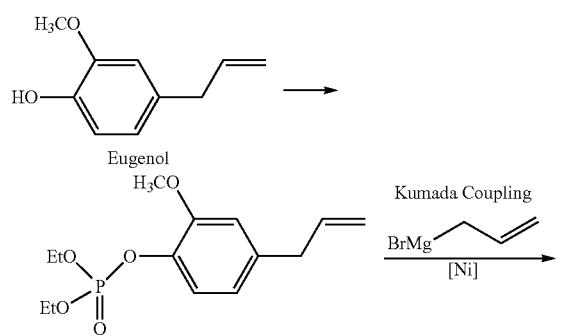

Lignin-derived compounds and derivatives thereof can be converted to intermediates that function as starting materials for monomer synthesis. The scheme below highlights some of the transformations which can be readily carried out using standard organic reactions to prepare monomers. For example, the symmetrical diallyl compound (1) can be converted to a dialdehyde using an oxidation (the process results in the loss of two carbon atoms) to produce a dialdehyde (2). Alternatively, It can be directly converted to a diacid (3) (also involves loss of two carbons). The diallyl compound can be converted to a diol (4) without the loss of any carbon atoms using a hydroboration protocol. The diol can be readily oxidized to the dialdehyde (5) or to the diacid (6) depending on the reaction conditions. Alternatively, treatment of the phosphonate (7) with vinyl Grignard reagent provides an unsymmetrical bisolefin which can serve as a precursor to produce unsymmetrical diols, dialdehydes, diacids or epoxides using a similar reaction sequence described above. The dialdehyde, for example (5), will provide the diamine (9) using a well investigated organic transformation, reductive amination.

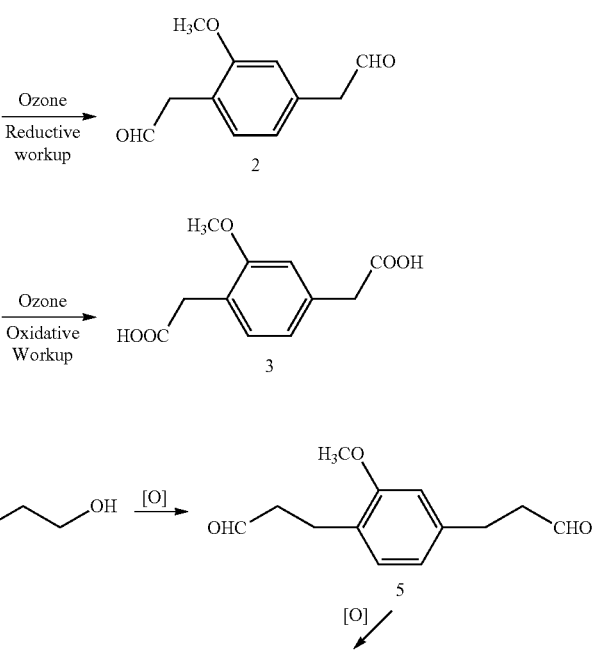

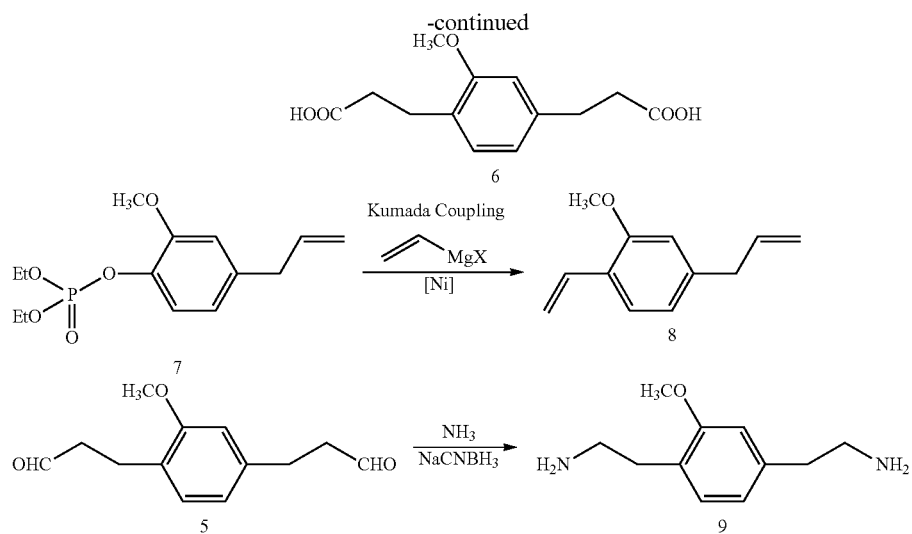

The different transformations described above can be readily extended to the synthesis of a variety of acid, alcohol, or amine monomers. Furthermore, we can introduce diversity into the products by choosing an appropriate lignin-derived starting material. The scheme below illustrates the potential application of biomass precursors to the synthesis of amines, alcohols, and acids.

The dialdehydes that are readily available from lignin derived precursors (vide supra) can be modified to incorporate additional carbons using either a Perkin or a Stobbe condensation, well known processes in organic synthesis. To showcase these transformations, we have utilized phthaldehydes as model compounds to incorporate additional carbons and prepare novel analogs of terephthalic acid. As

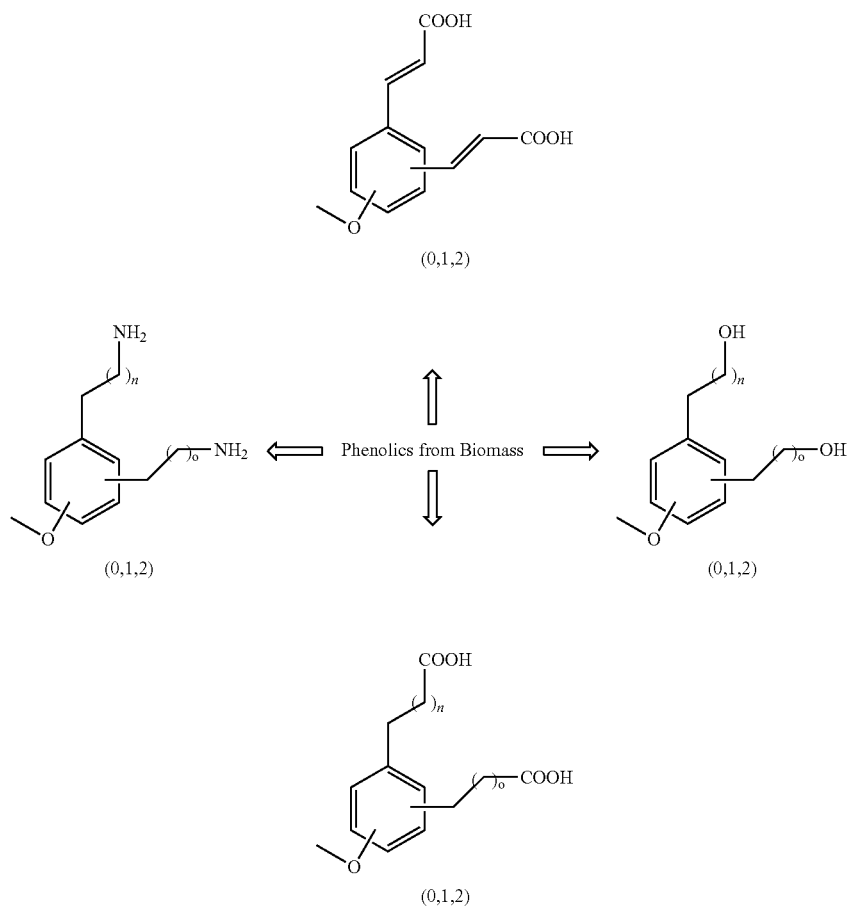

shown below, we can prepare diols and diacids readily starting from dialdehydes. We can easily adapt thesemethodologies for the synthesis of monomers derived from lignins.

The two schemes described below show how para and meta phthaldehydes can be converted to diacids and diols.

Reaction Scheme (1,4-Disubstituted Benzene):

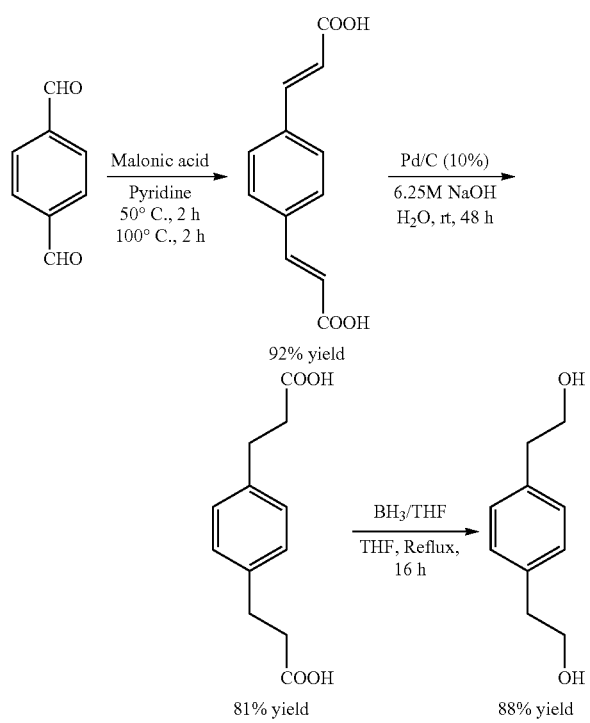

3,3'-(1,4-phenylene)bis-2-propenioc acid

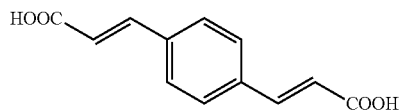 [SMILES: O=C(O)/C=C/c1ccc(/C=C/C(=O)O)cc1]

A mixture of malonic acid (32.6 g, 0.31 mol) and terephthalaldehyde (20 g, 0.14 mol) in pyridine (70 mL) was stirred at 50° C. for 2 h and 100° C. for 2.5 h. After cooling the reaction mixture was poured into sulfuric acid (275 mL, 1 M) and the white precipitate formed was filtered, washed with water and dried in vacuum to give 3,3'-(1,4-phenylene)bis-2-propenioc acid as white powder (30 g, 92%). $^1$H NMR (DMSO, 400 MHz) δ 6.5 (d, J=16 Hz, 2H), 7.5 (d, J=16 Hz, 2H), 7.7 (s, 4H); $^{13}$C NMR (DMSO, 100 MHz) δ 120.6, 129.1, 136.3, 143.4, 167.9; lit. mp: >300° C.

1,4-Benzenedipropanoic acid

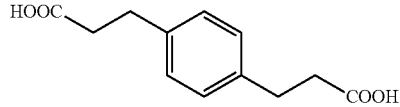 [SMILES: O=C(O)CCc1ccc(CCC(=O)O)cc1]

A modified literature approach was used (Bickley et al., New. J. Chem. 2004, 28, 425). 3,3'-(1,4-phenylene)bis-2-propenioc acid (10.0 g, 0.045 mol) and palladium on carbon (0.70 g, 10% w/w) was stirred in 6.25 M NaOH solution (15 mL) and water (70 mL) under hydrogen for 48 h. The catalyst was filtered using celite and the filtrate was acidified with conc. HCl. The white precipitate formed was filtered, washed with water and dried in vacuum to give product. The obtained product was purified from hot acetic acid to give pure 1,4-benzenedipropanoic acid as white powder (8.3 g, 81%). $^1$H NMR (DMSO, 400 MHz) δ 2.5 (t, J=7.6 Hz, 4H), 2.8 (t, J=7.6 Hz, 4H), 7.1 (s, 4H), 12.0 (s, 2H); $^{13}$C NMR (DMSO, 100 MHz) δ 30.4, 35.7, 128.6, 138.9, 174.2; lit. mp 228-230° C.

1,4-Benzenedipropanol

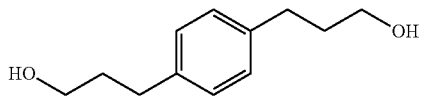 [SMILES: OCCCc1ccc(CCCO)cc1]

A modified literature approach was used (Ishichi et al., J. Bioorg. Med. Chem. 2013, 21, 4600). To the solution of 1,4-benzenedipropanoic acid (4.0 g, 18 mmol) in THF (80 mL) was added BH$_3$/THF (1 M) (81 mL, 81 mmol) at 0° C. The reaction mixture was slowly warmed to room temperature and refluxed for 16 h. Then mixture was cooled to 0° C. and quenched with saturated NH$_4$Cl solution and was extracted with ethyl acetate. The organic layer was washed with water, brine and dried over anhydrous Na$_2$SO$_4$. The combined organic layer was concentrated in vacuum to give 1,4-benzenedipropanol as white solid (3.5 g, 88%). $^1$H NMR (CDCl$_3$, 400 MHz) δ 1.8-1.9 (m, 4H), 2.6 (t, J=7.6 Hz, 4H), 3.6 (t, J=6.4 Hz, 4H), 7.0 (s, 4H); $^{13}$C NMR (CDCl$_3$, 100 MHz) δ 31.6, 34.2, 62.2, 128.4, 139.3.

Synthesis of m-Disubstituted Acids

Reaction Scheme (1,3-Disubstituted Benzene)

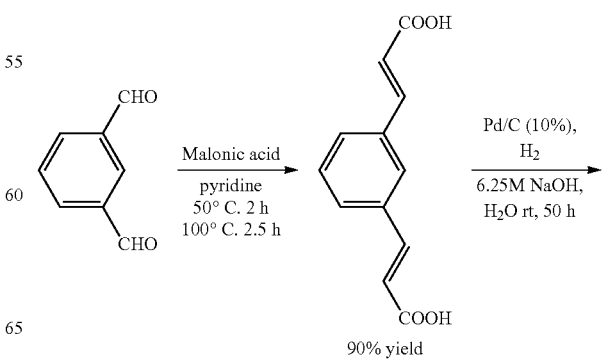

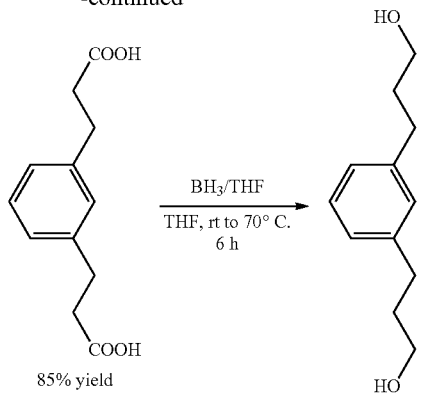

85% yield → 95% yield 3-(3-(2-carboxyvinyl)phenyl)prop-2-enoic acid

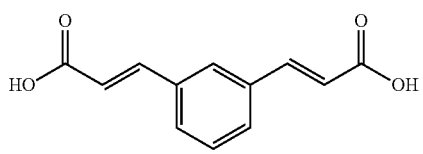 [SMILES: O=C(O)/C=C/c1cccc(/C=C/C(=O)O)c1]

A mixture of malonic acid (2.8 g, 27 mmol) and benzene-1,3-dicarboxaldehyde (1.2 g, 9 mmol) in pyridine (3.3 mL) was stirred at 50° C. for 2 h and 100° C. for 2.5 h. After cooling the mixture was poured into aqueous sulfuric acid (17 mL, 1 M) and the white precipitate filtered and dried to give as a white powder (90%). $^1$H NMR (CDCl$_3$, 400 MHz) δ 6.61 (d, J=16 Hz, 2H), 7.41 (t, J=7.6 Hz, 1H), 7.56 (d, J=16 Hz, 2H), 7.66 (dd, J=8, 1.6 Hz, 2H), 8.01 (s, 1H); $^{13}$C NMR (CDCl$_3$, 100 MHz) δ 120.8, 128.3, 130.1, 130.5, 135.6, 143.9, 168.1; lit. mp: 280-282° C.

3-(3-(2-carboxyethyl)phenyl)propanoic acid

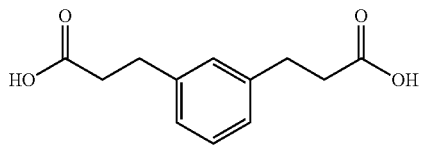 [SMILES: O=C(O)CCc1cccc(CCC(=O)O)c1]

A modified literature approach was used (Bickley et al., New. J. Chem. 2004, 28, 425). A sample of α,β-unsaturated diacid (2.18 mg, 10 mmol) was stirred in a mixture of aqueous degassed NaOH (2.5 mL, 6.25 M), degassed water (15 mL) and palladium on carbon (150 mg, 10% w/w) under hydrogen for 2.5 d. The catalyst was filtered off, and the reaction mixture acidified with conc. aqueous HCl, producing a white precipitate. Acetic acid (3.5 mL) was added and the mixture stirred at 80° C. for 20 min to dissolve the precipitate. On cooling a precipitate was formed again which was filtered off, washing with water, to give saturated diacid as white crystals (85%). $^1$H NMR (CDCl$_3$, 400 MHz) δ 2.47 (t, J=8 Hz, 4H), 2.75 (t, J=8 Hz, 4H), 6.99-7.05 (m, 3H), 7.14 (t, J=7.2 Hz, 1H); $^{13}$C NMR (CDCl$_3$, 100 MHz) δ 31.0, 35.9, 126.5, 128.8, 128.9, 141.5, 174.4; lit. mp 134-136° C.

3-(3-(3-hydroxypropyl)phenyl)propanol

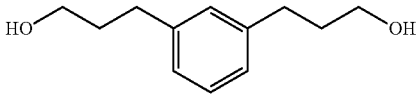 [SMILES: OCCCc1cccc(CCCO)c1]

A modified literature approach was used (Ishichi et al., J. Bioorg. Med. Chem. 2013, 21, 4600). To a solution of diacid (0.89 g, 4 mmol) in THF (12 mL) was added 1 M-BH$_3$/THF complex (24 mL, 24 mmol) at room temperature. After being stirred at 70° C. for 6 h, the mixture was quenched with water and aqueous NH$_4$Cl, extracted with EtOAc, washed with water and brine. The organic phase was dried over MgSO$_4$, concentrated in vacuo. The residue was purified by column chromatography to give diol as a colorless oil (95%). $^1$H NMR (CDCl$_3$, 400 MHz) δ 1.81-1.88 (m, 4H), 2.01 (br s, 2H), 2.65 (t, J=8 Hz, 4H), 3.62 (t, J=6.4 Hz, 4H), 6.98-7.02 (m, 3H), 7.17 (t, J=8 Hz, 1H); $^{13}$C NMR (CDCl$_3$, 100 MHz) δ 32.2, 34.4, 62.3, 126.1, 128.6, 128.9, 142.1.

Chain Length Extensions

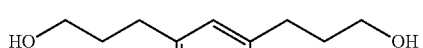

↓

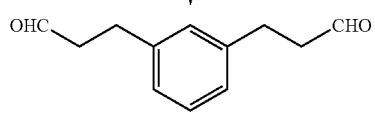

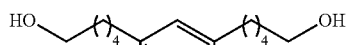

↑

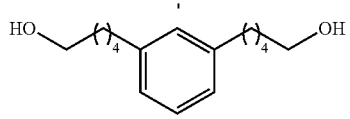

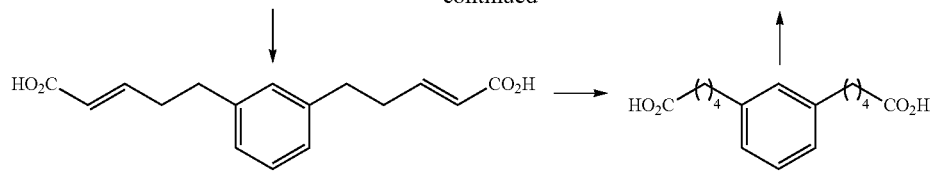

Synthesis of O-Allyleugenol and Derivatives

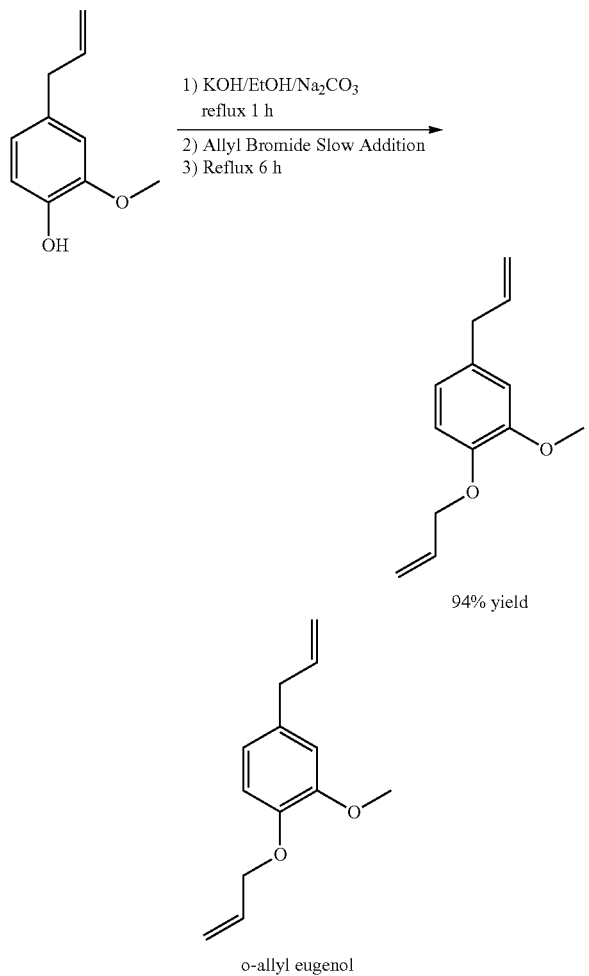

A 2.0 L single necked round bottomed flask was charged with potassium hydroxide (32 g, 0.57 mol), absolute ethanol (250 mL); the flask was capped and the hydroxide was shaken into solution. The combination was exothermic. To the alkaline ethanolic solution was added eugenol (87 mL, 0.50 mol). The solution turned dark green and gave a creamy solid precipitate. The mixture was capped and shaken up until it formed a uniform mash which gelled up. Additional absolute ethanol (250 mL) was added and the mix absorbed it into the mud. Additional absolute ethanol (250 mL) (making the total amount of ethanol equal to 750 mL) was added and the mixture broke loose upon shaking to afford a light tan slurry. Sodium carbonate (10.6 g, 0.10 mol) was added and the mixture was heated to reflux until all but the sodium carbonate dissolved (circa 1 h). The mixture was allowed to cool enough so that it was no longer boiling. In a well ventilated fume hood, allyl bromide (48 mL, 0.55 mol) was measured out into a graduated cylinder. The allyl bromide was poured slowly directly into the stirring reaction mixture. The combination was quite exothermic and frequent breaks in the addition were made to allow the mixture to cool below the boiling point again. Absolute ethanol (50 mL) was used to rinse the residual allyl bromide into the reaction. The solution had become pregnant with white crystalline solid. The mixture was refluxed for one and a half hours when most of the orange color had dispersed from the solution. The mixture was refluxed for an additional three hours. The mixture was allowed to cool. The amber solution was isolated from the white solid precipitate by suction filtration through qualitative paper, and then the filtrate was concentrated by rotary evaporation under vacuum induced by a water aspirator. The residue was partitioned between diethyl ether (300 mL) and aqueous sodium hydroxide (200 mL of 100 mL 50% wt NaOH diluted to 600 mL) in a 1.0 L separatory funnel. The ethereal solution was washed with aqueous sodium hydroxide (2×200 mL of the previously prepared solution), saturated sodium chloride (200 mL), and isolated. The amber ethereal solution was dried (anhydrous sodium sulfate), isolated by gravity filtration through cotton, and then concentrated by rotary evaporation under vacuum induced by a water aspirator. The golden oil was stored under high vacuum overnight to afford o-allyl eugenol (96.2 g, 94% yield).

$^1$H NMR (CDCl$_3$, 400 MHz) δ: 3.37 (d, J=6.8 Hz, 2H), 3.89 (s, 3H), 4.62 (d, J=5.6 Hz, 2H), 5.10 (m, 2H), 5.16 (d, J=17.2 Hz, 1H), 5.41 (d, J=16.0 Hz, 1H), 6.0 (m, 1H), 6.12 (m, 1H), 6.75 (m, 2H), 6.84 (d, J=8 Hz, 1H)

$^{13}$C NMR (CDCl$_3$ 100 MHz) δ: 39.8, 55.9, 70.0, 112.3, 113.7, 115.6, 117.8, 120.1, 143.1, 133.6, 137.7, 146.4, 149.4

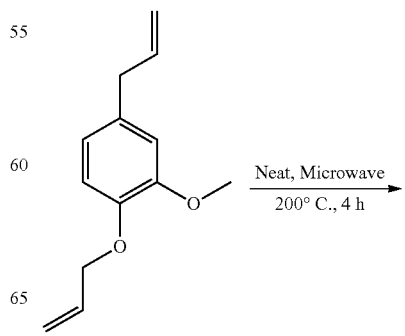

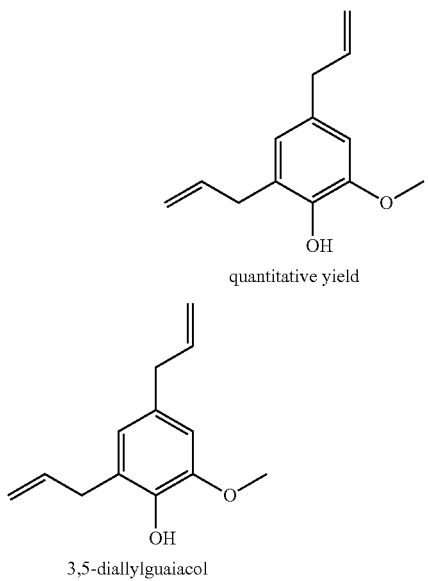

quantitative yield 3,5-diallylguaiacol

A disposable microwave reaction vial was charged with o-allyl eugenol (4.4 g, 0.022 mol) and a PTFE coated magnetic spin bar. A disposable septum was crimped onto the top of the vial which was then placed into the microwave reactor. The mixture was set as a medium absorber of microwaves in the quick setup menu. The reactor was set to heat the sample to 200° C. for four hours. The septum was pulled off with a pliers and a sample of the mixture was pulled for NMR analysis. The conversion was quantitative with no purification and afforded 3,5-diallylguaiacol as a golden oil.

$^1$H NMR (CDCl$_3$, 400 MHz) δ: 3.35 (d, J=6.8 Hz, 2H), 3.44 (d, J=6.8 Hz, 2H), 3.91 (s, 3H), 5.1 (m, 4H), 5.63 (s, 1H), 6.05 (m, 2H), 6.63 (s, 2H)

$^{13}$C NMR (CDCl$_3$ 100 MHz) δ: 33.9, 40.0, 56.0, 109.0, 111.1, 114.3, 115.4, 115.5, 115.5, 121.2, 122.1, 125.6, 131.1, 136.7, 137.9, 141.6, 146.3

The complete disclosures of all patents, patent applications including provisional patent applications, publications including patent publications and nonpatent publications, and electronically available material cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A compound according to formula II:

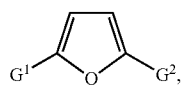

(II)

wherein both G$^1$ and G$^2$ are independently

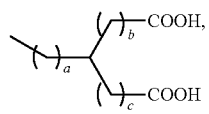

and where a is 1, 2 or 3; and b and c are independently 0, 1, 2, or 3.

2. The compound according to claim 1, wherein at least one of b and c in both G$^1$ and G$^2$ are 0.

3. The compound according to claim 1, wherein only one of b and c in both G$^1$ and G$^2$ are 0.

4. The compound according to claim 1, wherein the structure of G$^1$ and G$^2$ are the same.

5. The compound according to claim 1, wherein the compound of formula II is selected from:

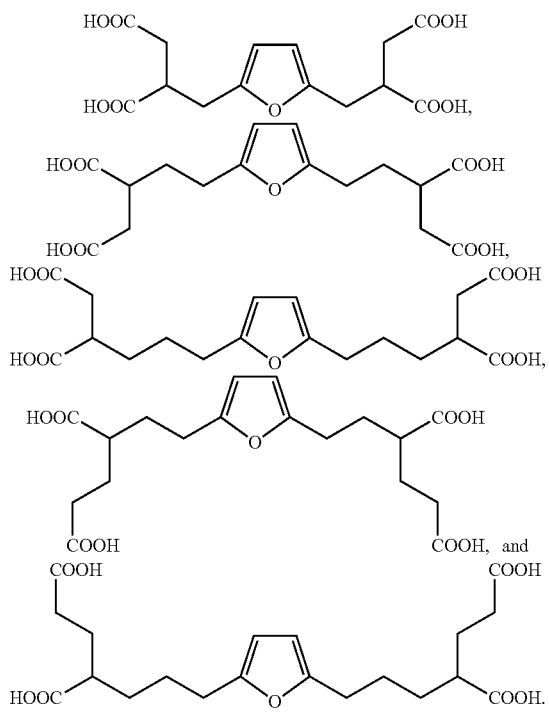

6. A compound according to formula II:

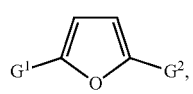

(II)

wherein one of G$^1$ and G$^2$ is —(CH$_2$)$_d$OH, wherein d is 1, 2, 3, 4 or 5, and the other of G$^1$ and G$^2$ is

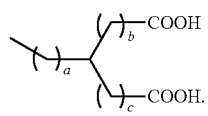

where a is 1, 2 or 3; and b and c are independently 0, 1, 2, or 3,

—(CH$_2$)$_d$OH where d is 1, 2, 3, 4 or 5, or
—(CH$_2$)$_e$COOH where e is 0, 1, 2, 3, 4 or 5.

7. The compound according to claim 6, wherein one of G$^1$ and G$^2$ is —(CH$_2$)$_d$OH, wherein d is 1, 2, 3, 4 or 5, and the other of G$^1$ and G$^2$ is

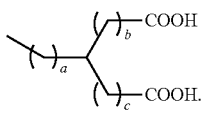

8. The compound according to claim 6, wherein the compound of formula II is:

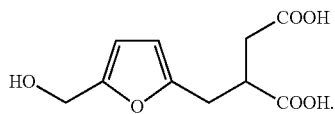 [SMILES: O=C(O)CC(Cc1ccc(CO)o1)C(=O)O]

9. A compound according to formula II:

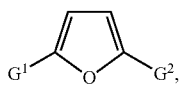

(II)

wherein both G$^1$ and G$^2$ are independently —(CH$_2$)$_e$COOH where e is 0, 1, 2, 3, 4 or 5,
with the caveat that if both G$^1$ and G$^2$ are —(CH$_2$)$_e$COOH and one of e is 2 then the other e is not 0 or 2 and with the caveat that the compound according to formula II is asymmetric.

10. The compound according to claim 9, wherein the compound of formula II is selected from:

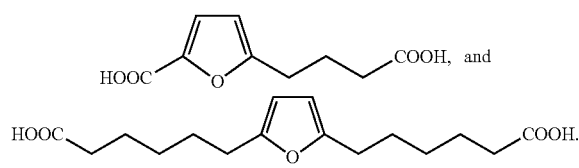

11. The compound according to claim 1 derived from cellulose, hemicellulose or a combination thereof.

12. The compound according to claim 1 derived from fructose, cellulose, hemicellulose or a combination thereof.

13. The compound according to claim 12, wherein the fructose is dehydrated to form 5-hydroxymethylfurfural (HMF).

14. The compound according to claim 1, wherein the compound of formula II is polymerized.

15. The compound according to claim 14, wherein the polymerization comprises free radical polymerization.

16. The compound according to claim 14, wherein the polymer is a nylon, a polyester, a polyurethane, a polyamide, or a combination thereof.

17. The compound according to claim 14, wherein the polymer can be used as an adhesive, a plastic, a thermoplastic, a gel, a coating, a film, or any combination thereof.

18. The compound according to claim 6, derived from cellulose, hemicellulose or a combination thereof.

19. The compound according to claim 6 derived from fructose, cellulose, hemicellulose or a combination thereof.

20. The compound according to claim 19, wherein the fructose is dehydrated to form 5-hydroxymethylfurfural (HMF).

21. The compound according to claim 6, wherein the compound of formula II is polymerized.

22. The compound according to claim 21, wherein the polymerization comprises free radical polymerization.

23. The compound according to claim 21, wherein the polymer is a nylon, a polyester, a polyurethane, a polyamide, or a combination thereof.

24. The compound according to claim 21, wherein the polymer can be used as an adhesive, a plastic, a thermoplastic, a gel, a coating, a film, or any combination thereof.

25. The compound according to claim 9, derived from cellulose, hemicellulose or a combination thereof.

26. The compound according to claim 9 derived from fructose, cellulose, hemicellulose or a combination thereof.

27. The compound according to claim 26, wherein the fructose is dehydrated to form 5-hydroxymethylfurfural (HMF).

28. The compound according to claim 9, wherein the compound of formula II is polymerized.

29. The compound according to claim 28, wherein the polymerization comprises free radical polymerization.

30. The compound according to claim 28, wherein the polymer is a nylon, a polyester, a polyurethane, a polyamide, or a combination thereof.

31. The compound according to claim 28, wherein the polymer can be used as an adhesive, a plastic, a thermoplastic, a gel, a coating, a film, or any combination thereof.

* * * * *

UNITED STATES PATENT AND TRADEMARK OFFICE
CERTIFICATE OF CORRECTION

PATENT NO. : 11,220,475 B2
APPLICATION NO. : 16/722710
DATED : January 11, 2022
INVENTOR(S) : Mukund P. Sibi Page 1 of 1

It is certified that error appears in the above-identified patent and that said Letters Patent is hereby corrected as shown below:

In the Claims

In Column 76, Line 1 (Claim 1): the term 'G" should read --$G^1$--.

In Column 76, Line 1 (Claim 1): the term 'CT" should read --$G^2$--.

Signed and Sealed this
First Day of April, 2025

Coke Morgan Stewart
*Acting Director of the United States Patent and Trademark Office*